(12) United States Patent
Carey

(10) Patent No.: US 9,469,622 B2
(45) Date of Patent: Oct. 18, 2016

(54) PROCESS FOR THE CYCLODEHYDRATION OF DIOLS AND USE THEREOF FOR THE MANUFACTURING OF AMBRAFURAN AND OTHER CYCLOETHER DERIVATIVES

(75) Inventor: Charles Carey, Paris (FR)

(73) Assignee: KOSTE BIOCHEMICALS SAS, Paris (FR)

( * ) Notice: Subject to any disclaimer, the term of this patent is extended or adjusted under 35 U.S.C. 154(b) by 0 days.

(21) Appl. No.: 14/232,464

(22) PCT Filed: Jul. 13, 2012

(86) PCT No.: PCT/EP2012/063854
§ 371 (c)(1),
(2), (4) Date: Mar. 14, 2014

(87) PCT Pub. No.: WO2013/007832
PCT Pub. Date: Jan. 17, 2013

(65) Prior Publication Data
US 2014/0199741 A1   Jul. 17, 2014

Related U.S. Application Data

(60) Provisional application No. 61/590,075, filed on Jan. 24, 2012.

(30) Foreign Application Priority Data

Jul. 13, 2011 (EP) .................................. 11173870

(51) Int. Cl.
| | | |
|---|---|---|
| C07D 307/92 | (2006.01) | |
| C07C 29/149 | (2006.01) | |
| C07C 29/76 | (2006.01) | |
| B01J 19/24 | (2006.01) | |
| C07D 311/58 | (2006.01) | |
| C07D 311/70 | (2006.01) | |
| C12P 7/22 | (2006.01) | |
| C12P 7/02 | (2006.01) | |
| C12P 17/04 | (2006.01) | |

(52) U.S. Cl.
CPC ............. *C07D 307/92* (2013.01); *B01J 19/24* (2013.01); *C07C 29/149* (2013.01); *C07C 29/76* (2013.01); *C07D 311/58* (2013.01); *C07D 311/70* (2013.01); *C12P 7/02* (2013.01); *C12P 7/22* (2013.01); *C12P 17/04* (2013.01); *C07C 2101/18* (2013.01); *Y02P 20/544* (2015.11); *Y02P 20/582* (2015.11)

(58) Field of Classification Search
CPC ................................................... C07D 307/92
See application file for complete search history.

(56) References Cited

U.S. PATENT DOCUMENTS

| 3,029,255 A | 4/1962 | Stoll |
|---|---|---|
| 4,798,799 A | 1/1989 | Farbood et al. |
| 4,970,163 A | 11/1990 | Farbood et al. |
| 5,670,670 A | 9/1997 | Knuebel et al. |
| 5,945,546 A | 8/1999 | Subbiah |
| 2010/0248316 A1* | 9/2010 | Steenkamp .......... C07D 307/92 435/126 |

FOREIGN PATENT DOCUMENTS

JP    61-33184 A    2/1986

OTHER PUBLICATIONS

Kotka et al. J. Chem. Soc. Pekin Trans., 1988, 1749-1752.*
Richter et al. Chem. Eng. Technol., 2001, 24(4):340-343.*
International Search Report, dated Aug. 2, 2012, from corresponding PCT application.

* cited by examiner

*Primary Examiner* — Bin Shen

(57) ABSTRACT

A process for manufacturing tetrahydrofuran, tetrahydropyran and, more generally, cycloether derivatives through the cyclodehydration of 1,4- or 1,5-diols. More specifically, the process of the invention involves (i) the stereoselective cyclodehydration in water of 1,4- or 1,5-diols including at least one chiral tertiary alcohol functional group with retention of the initial chirality, and/or (ii) the cyclodehydration in water of 1,4- or 1,5-diols, said diols being non-miscible with and/or non-soluble in water, into corresponding cycloether derivatives, by bringing the reaction mixture to high temperature water (HTW) conditions and/or by mixing the aqueous reaction mixture with a solid catalyst, such as for example a smectite clay. Also, the use of the process for manufacturing ambrafuran, especially (−)-ambrafuran and other cycloether derivatives.

15 Claims, 16 Drawing Sheets

PROCESS FOR THE CYCLODEHYDRATION OF DIOLS AND USE THEREOF FOR THE MANUFACTURING OF AMBRAFURAN AND OTHER CYCLOETHER DERIVATIVES

FIELD OF INVENTION

The present invention relates to a process for manufacturing tetrahydrofuran, tetrahydropyran and, more generally, cycloether derivatives through the cyclodehydration of 1,4- or 1,5-diols. More specifically, the process of the invention involves
(i) the stereoselective cyclodehydration in water of 1,4- or 1,5-diols comprising at least one chiral tertiary alcohol functional group (such diols being referred to thereafter as the "Chiral Diols") with retention of the initial chirality, and/or
(ii) the cyclodehydration in water of 1,4- or 1,5-diols, said diols being non-miscible with and/or non-soluble in water (such diols being referred to thereafter as the "Non-Soluble Diols" and together with Chiral Diols the "Targeted Diols"),
into corresponding cycloether derivatives,
by bringing the reaction mixture to high temperature water (HTW) conditions and/or by mixing the aqueous reaction mixture with a solid catalyst, such as for example a smectite clay.

The present invention further relates to the use of the process of the invention for manufacturing ambrafuran, especially (−)-ambrafuran and other cycloether derivatives. More specifically, the present invention further pertains to a process for manufacturing products of interest selected from the group comprising decahydro-2-hydroxy-2,5,5,8a-tetramethylnaphthalene-1-ethanol (thereafter "ambradiol"), sclareolide and ambrafuran, comprising a step of biological conversion of sclareol and at least a further catalytic step performed in water medium.

BACKGROUND OF INVENTION

A. Chiral Cycloether Derivatives
A.1. Cyclodehydration Reaction

The use of cyclodehydration reactions is of importance in the chemical industry. This kind of reaction is, for example, widely used for the production of tetrahydrofuran from 1,4-butanediol and, more generally, for the production of various cycloethers.

One of the most cost-effective and atom-efficient processes for producing cycloethers is through the acid-catalyzed dehydration of alcohols. This reaction is usually carried out in liquid phase. The acid-catalyzed cyclodehydration yet presents the following drawbacks:
- possibility of rearrangements of alcohols from primary to secondary alcohols, thereby giving mixtures of products,
- requirement of separation and neutralization steps when the acid catalyst is in homogeneous phase,
- production in batch or semi-batch reactors when using homogeneous catalysts and not in continuous flow reactors,
- formation of thermodynamic and kinetic products due to long residence time in the reactor,
- possible isomerization of chiral compounds due to acid conditions.

Of all the abovementioned issues, the isomerization of chiral compounds into a mixture of stereoisomers is of particular concern. Indeed, the separation of different isomers constitutes a challenging task involving several steps, substantial product loss and extra costs that could be avoided by using a stereoselective synthesis pathway in the first place.

The issue of chirality is especially relevant when performing the cyclodehydration of 1,4- and 1,5-diols in the particular case when one of the two alcohols is a chiral tertiary alcohol and the second one is a primary alcohol. Given that tertiary alcohols are known to be more reactive to acid-catalyzed dehydration than primary or secondary alcohols, the dehydration of the chiral tertiary alcohol during the acid-catalyzed cyclodehydration process takes place readily through the formation of a carbocation, thereby disrupting the chiral configuration at the tertiary alcohol stereocenter. The cyclization that ensues therefore generates a mixture of isomers and most often of enantiomers.

An example of such issue can be found in the thesis of Allemann C., "*Synthesis and Application of an Electronically Chiral Mimic of CpFe*", 2002, where the cyclodehydration of ambradiol to (−)ambrafuran under acidic conditions is said at page 33 to yield a racemic mixture of (−) and (+) ambrafuran (Scheme 1 below). Regarding the reasons of such isomerization, Allemann C. writes further that "the configuration at C-8 needs to be preserved during the intramolecular nucleophile substitution of the tertiary alcohol on the C-12 that bears the primary alcohol. Thus, the elimination of the 8-hydroxyl group must be prevented".

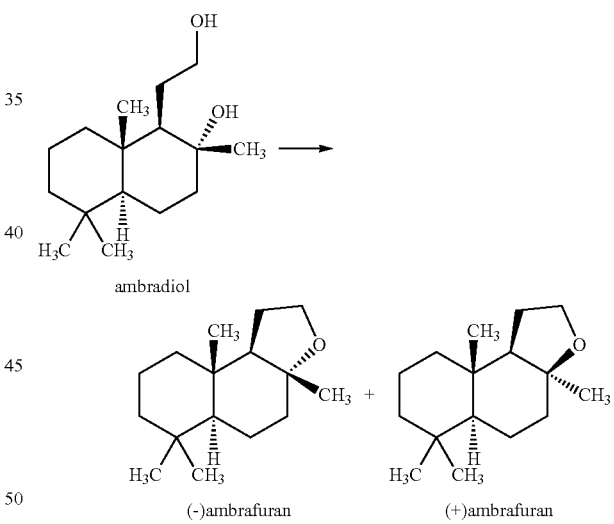

Scheme 1

Similarly, among other methods known to the art, one way to avoid the loss of the chiral configuration in the cyclodehydration of a diol when one of the two alcohols is a chiral tertiary alcohol and the other one is primary or secondary, consists in converting such primary or secondary alcohol into a better leaving group such as a mesylate, tosylate, methoxy methyl ether, phosphite ester or chlorosulfite group. Cyclization, usually under basic conditions, then takes place by attack from the tertiary alcohol on the substituted group, thereby preserving the original chiral configuration. Alternatively, $ZnCl_2$ may be used to prevent elimination of the 8-hydroxyl group. However, such methods are not atom-efficient, result in chemical waste, use organic solvents of petrochemical source that contribute to increasing the environmental impact and energy cost of such transformations, use reagents that need to be separated from the final product and more generally contribute to high processing time and costs.

Therefore, there is a need for an improved stereoselective process for the cyclodehydration of Chiral Diols or Non-Soluble Diols.

A.2. Stereoselective Cyclodehydration Using Solid Catalysts

U.S. Pat. No. 3,029,255 and JP-A-86/33184 describe processes for the cyclization of ambradiol into (−)-ambrafuran using β-naphtalene sulphonic acid, alumina, bleaching earth, alumina or silica as catalysts. However, such methods generate undesirable secondary products, isomers around the $8^{th}$ carbon stereocenter and result in low yields, generally below 70%.

U.S. Pat. No. 5,670,670 describes a process for the cyclization of ambradiol into (−)-ambrafuran using montmorillonite clay K catalysts with an acid charge below 80 or 100 mval at a temperature between 20° C. and 130° C.

Among smectite clays, montmorillonite and bentonites (together "MTM") are defined by a layered structure formed by tetrahedral and/or octahedral sheets of approximate formula: $M_x^+(Si_{4-y}Al_y)[(Al,Fe^{3+})_{2-z}(Mg,Fe^{2+})_z]O_{10}(OH)_2 \cdot nH_2O$ where x=[0.2-0.6], x=y+z and y<<z.

MTMs are characterized as crystalline aluminosilicates with a large surface area while containing various other cations. They have been used as solid Bronsted and Lewis acid catalysts in their natural and ion-exchanged form to perform reactions such as ether or anhydride formation, esterification, Diels-Alder addition, rearrangements, oxidation-reduction and formylation. Also, MTMs have been successfully used for the dehydration of tertiary alcohols at moderate temperatures.

However, the method described in U.S. Pat. No. 5,670,670 requires the use of an organic solvent to solubilize the ambradiol, separation between the catalyst and the solvent containing the ambrafuran, further solvent drying and requires water content remaining below 2% for the cyclodehydration to take place, which conflicts with the release of water during the cyclo-dehydration process.

Patent application US2010/0248316 proposes an enantioselective cyclodehydration method consisting in exposing ambradiol to an activated zeolite at a temperature between 0° C. and 110° C. for a period of between 1 and 24 hours. This method allows the enantioselective cyclodehydration of the diol into (−)-ambrafuran. In this patent application, the cyclodehydration of ambradiol on activated zeolite is carried out in hexane or in toluene at room temperature or in dimethylsulfoxyde (DMSO) or ethyl acetate, optionally heating the solution. At the end of the reaction, solvent should be removed under reduced pressure.

Zeolites are aluminosilicates, which are well known as solid catalysts. The main features of these materials are their channel dimensions and stable structures. Their use in industrial processes generally results in a reduction in waste and pollution. The zeolite used in patent application US2010/0248316 is a Group IIA metal zeolite, with calcium as metal.

In most situations, zeolites need to be activated before being used as catalysts, especially by removing from active sites water or other small molecules that may have been adsorbed. In US2010/0248316, one treatment consists in a reflux treatment at 90° C. for 24 hours in presence of ammonium nitrate. Another treatment is activation at 500° C. under vacuum or with a conventional microwave oven. After treatment, the activated zeolite should be kept in a closed container before use to avoid inactivation through contact with ambient air.

Several drawbacks remain when trying to apply US2010/0248316 to the stereoselective cyclodehydration of Chiral Diols or Non-Soluble Diols. One of them is the use of specific organic solvents to carry out the cyclodehydration reaction and to extract and purify the resulting product. Specifically, during the cyclodehydration step, only toluene and hexane are claimed to afford 100% conversion rate in 4 hours at room temperature while ethanol or ethyl acetate afford conversion rates of only 5.4% and 3.7% respectively. The cost of solvents, the manipulations needed as well as the evaporation steps are not optimal. Moreover, solvent use often results in atmospheric contamination during drying steps or disposal of spent material and may contaminate the final product, which is not environmentally friendly, requires costly recycling processes and may constitute health risks for consumers.

Another drawback of the method described in patent application US2010/0248316 is that the conversion requires between 1 and 4 hours to proceed fully.

Yet, another drawback of the method of patent application US2010/0248316 is the restrictive activation step of the zeolite performed at high temperature. The treatment described for zeolite activation further rules out the establishment of a fully continuous production process. Moreover, the manipulation of the activated zeolite from the drying site to the dehydration site automatically induces a partial inactivation of the zeolite through air contact, which in turn results in using a higher ratio of zeolite to ambradiol. In order to avoid zeolite inactivation and zeolite recharging, use would have to be performed in controlled airtight atmosphere, which inevitably contributes to generating extra costs compared to a minimal setup. Another drawback is the potential coking of the zeolite that may take place during reactivation at 500° C.

Also, zeolites have the capacity to catalyze a wide range of undesirable reactions such as dehydrogenation, esterification or Diels-Alder reactions. Specifically, time-dependent ambrafuran isomerization was also observed when using CBV320A during the dehydration of ambradiol. This implies the need for very strict control of reaction time and it seems impossible to avoid minimal isomer formation during the reaction.

A.3. Cyclodehydration of Targeted Diols Using HTW

The Applicant investigated the feasibility of performing (i) the stereoselective cyclodehydration of Chiral Diols into corresponding cycloether derivatives while retaining the initial chirality and/or (i) the cyclodehydration of Non-Soluble Diols into corresponding cycloether derivatives, in either case in a pressure-controlled and heated vessel containing HTW, optionally fed with supercritical fluids and gases such as $CO_2$ and/or $N_2$, surfactants, catalysts and other additives.

It was previously shown that the reversible cyclodehydration of 1,4-butanediol into tetrahydrofuran may be carried out in HTW (Richter T. and Vogel H., Chem. Eng. Technol., 2001, 24, 340-343; Hunter S., Ehrenberger C. and Savage P., J. Org. Chem., 2006, 71, 6229-6239). At the temperature and pressure conditions used in these references, the authors showed that the cyclodehydration of 1,4-butanediol into tetrahydrofuran is acid-catalyzed by $H_2O$ serving directly as a proton donor and/or by native H+ ions. Therefore, these conditions were never envisaged for the stereoselective synthesis of chiral cycloether derivatives from Chiral Diols as acid-catalyzed cyclodehydration is known to imply isomerization in such molecular configurations.

According to the Applicant's knowledge, no specific information can be found in prior art regarding the transformation using HTW of Chiral Diols into corresponding cycloether derivatives with retention of the initial chirality or regarding the cyclodehydration of Non-Soluble Diols.

The Applicant however carried tests using a pressure-controlled vessel containing HTW and surprisingly found that Chiral Diols could be irreversibly and stereoselectively cyclodehydrated into a corresponding cycloether derivative while retaining the original chirality and/or that Non-Soluble Diols could be irreversibly cyclodehydrated into a corresponding cycloether derivative, using HTW, preferably mixed with a supercritical fluid and/or gas such as $CO_2$ and/or $N_2$ and/or other additives, preferably while stirring such a mixture between 10 and 1500 rpm and/or while homogenizing the mixture with methods known to the art such as ultrasonication or homogenization and/or optionally in combination with other solvents, catalysts and/or surfactants. Moreover, it was found that temperatures and/or pressures below the ones described by Hunter et al. were efficient to carry out the cyclodehydration. In one embodiment, it was also found that in the conditions of the present invention, the cyclodehydration may be irreversible and therefore total conversion may be expected contrary to what was described in the prior art.

The stereoselectivity of the cyclodehydration reaction in HTW as well as the ability to perform such transformations regardless of the diol solubility in or miscibility with HTW were both surprising.

Indeed, in the case of Non-Soluble Diols, the heterogeneous catalytic dehydration of diols in HTW had not been found in prior art and could not be expected to take place. In the case of Chiral Diols, as mentioned above, it was shown that dehydration in HTW occurs through an acid catalysis involving protonation of the alcohol function and carbocation formation. Therefore, the cyclodehydration in HTW of Chiral Diols should have inevitably resulted in the disruption of the chiral configuration at the tertiary alcohol carbon site and thereby in the production of a mixture of isomers. Instead, in the present invention, using temperatures and pressures quite lower than in Hunter et al. and Richter et al surprisingly resulted in completely avoiding isomerization. Without willing to be bound by any theory, it is thought that at these temperatures and pressures, the cyclodehydration of Chiral Diols catalyzed by HTW may involve the linking of a hydrogen atom from a water molecule with the oxygen atom of the relevant tertiary alcohol in the substrate, such tertiary alcohol being positioned at the water-substrate interface in the case of non-HTW soluble compounds, thereby triggering a cyclodehydration mechanism. However, at these temperatures and pressures, the dehydration mechanism is not yet fully understood.

A.4. Cyclodehydration of Targeted Diols in Water Over a Solid Catalyst Such as for Example K-Type Montmorillonite Clay Furthermore, the Applicant investigated the feasibility of performing in water at temperatures below HTW conditions (i) the stereoselective cyclodehydration of Chiral Diols into corresponding cycloether derivatives while retaining the initial chirality and/or (ii) the cyclodehydration of Non-Soluble Diols into corresponding cycloether derivatives, in both cases using a solid catalyst such as for example K-type montmorillonite, optionally ion-exchanged with a Class I or Class II metal or charged with Hydrogen.

The Applicant carried further experiments using montmorillonite clays and surprisingly found that Chiral Diols could be cyclo-dehydrated into their corresponding chiral cycloether derivative with retention of the initial chirality and/or that Non-Soluble diols could be cyclo-dehydrated into their corresponding cycloether derivative, in both cases in water medium over K-type montmorillonites where the total water weight content of the mixture is higher than 3%, preferably while stirring such a mixture and/or subjecting it to ultrasonication and/or optionally in combination with other solvents, catalysts and/or surfactants.

These findings are particularly surprising given that the absence of solubilization of a substrate in an appropriate solvent is known to increase mass transfer resistance in heterogeneous catalysis and should result in poor catalytic activity. Such findings are even more surprising given that high concentrations of water on the surface of montmorillonite are expected to reduce the activity of the dehydration catalyst. In that respect, U.S. Pat. No. 5,670,670 writes specifically that the water content of the reaction mixture should not be higher than 2% for the dehydration to take place. Furthermore, the addition of montmorillonite clays to water could be expected to increase Bronsted-type acidity, which would result in carbocation formation in place of the tertiary alcohol and in the subsequent isomerization of the final product.

A.5. Cyclodehydration of Targeted Diols in HTW Over a Solid Catalyst Such as for Example K-Type Montmorillonite Clay The applicant surprisingly found that combining HTW with a solid catalyst such as for example K-type montmorillonites allowed to perform (i) the stereoselective cyclodehydration of Chiral Diols into corresponding cycloether derivatives while retaining the initial chirality and/or (ii) the cyclodehydration of Non-Soluble Diols into corresponding cycloether derivatives, in substantially shorter reaction times and/or with higher product selectivity than either using HTW alone or a solid catalyst such as for example K-type montmorillonites in water or in an organic solvent such as hexane. More specifically, using HTW in combination with a solid catalyst such as for example K-type montmorillonites allowed to improve the stereoselective cyclo-dehydration of ambradiol into (−)-ambrafuran from a yield of approximately 92.5% in 3.5 hours in pure HTW to a yield of 98% in 10 minutes in HTW mixed with montmorillonites.

Therefore, a solution found by the Applicant to operate the (i) the stereoselective cyclodehydration of Chiral Diols into corresponding cycloether derivatives with retention of the initial chirality and/or (ii) the cyclodehydration of Non-Soluble Diols into corresponding cycloether derivatives comprises performing such reaction using HTW, a solid catalyst such as for example K-type montmorillonites or a mixture thereof, preferably while keeping the total water weight content of the mixture above 3% in all operating conditions (see scheme 2 below).

Scheme 2

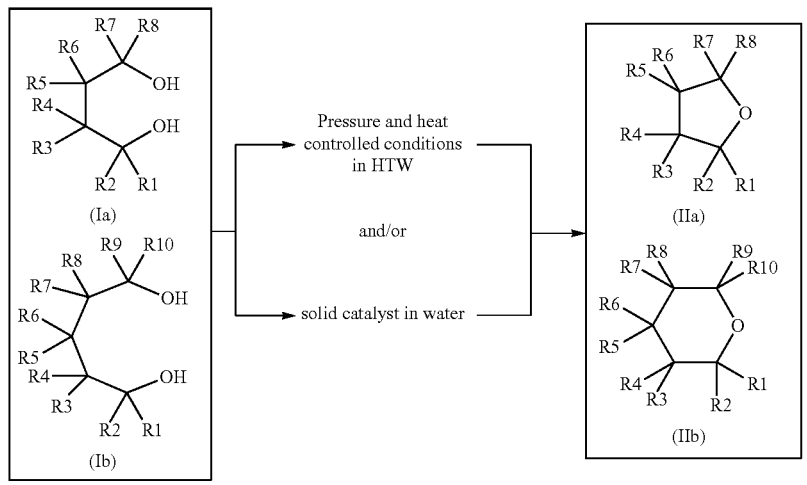

Using HTW and/or a solid catalyst such as for example K-type montmorillonites in the present invention for performing the cyclodehydration of Chiral and/or Non-Soluble Diols, presents the following further advantages:
- avoiding the use of conventional organic solvents and hence providing environmental benefits,
- avoiding the use of chemical reactants and reducing the need to recharge catalysts at high temperatures between 300° C. and 550° C.,
- when diols are not miscible with water, allowing their separation from water by simple decanting, centrifugation or filtration, thereby potentially avoiding drying, purification and solvent extraction steps,
- making it possible to perform the transformation in a continuous process, thereby allowing for reduced processing time and fewer transformation steps.

B. Manufacturing of Ambrafuran

The Applicant found that one substrate of particular interest that can be synthesized by the process of the invention using a cyclodehydration step under HTW conditions and/or through contact with a solid catalyst such as for example K-type montmorillonite in water is dodecahydro-3a,6,6,9a-tetramethylnaphto[2,1-b]furan, also called ambrafuran, preferably (−)-ambrafuran.

Ambrafuran is marketed by Firmenich S.A. under the trademark Ambrox® and is an important fragrance chemical. This molecule, and especially (−)-ambrafuran, its Laevo isomer (3aR,5aR,9aS,9bS)-3a,6,6,9a-tetramethyl-dodecahydronaphto[2,1-b]furan, is responsible for the characteristic odor of ambergris—a naturally occurring amber note with a rich woody character—and is used as a fixative agent in perfumes. This fragrance is used in perfumery but also increasingly in hygiene products or detergents. The production of ambrafuran including its isomers is estimated to about 200 tonnes/year.

Ambergris is a metabolic substance produced in the digestive track of the sperm whale. When expelled from the whale, ambergris floats at the surface of the sea, being exposed to air and sunlight. These conditions led to changes in the substance and are essential to the development of the fragrance. Due to its origin, natural ambergris is extremely rare. Moreover, its commercial exploitation has been forbidden by the Washington Treaty.

B.1. Known Syntheses of (−)-Ambrafuran

Due to the value of ambergris, extensive research has been conducted to analyze its composition, revealing the importance of ambrafuran and especially its (−)-ambrafuran isomer. Several routes of chemical synthesis of (−)-ambrafuran were therefore explored.

Total syntheses were developed as well as hemi-syntheses, starting from naturally occurring sesqui- or di-terpens such as sclareol, a compound extracted from *Salvia sclarea* (clary sage).

The main drawback of these syntheses is the high number of steps needed to obtain ambrafuran, usually eight steps from sclareol as reported in US patent application US2010/0248316. The last steps of the chemical synthesis are reported below (scheme 3), showing the synthesis of the intermediate products sclareolide and ambradiol:

Scheme 3

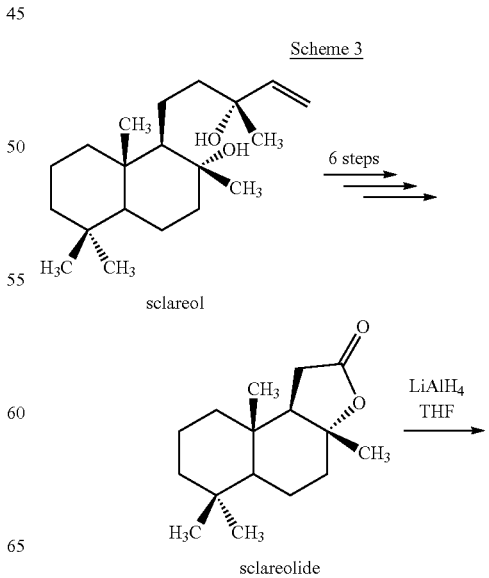

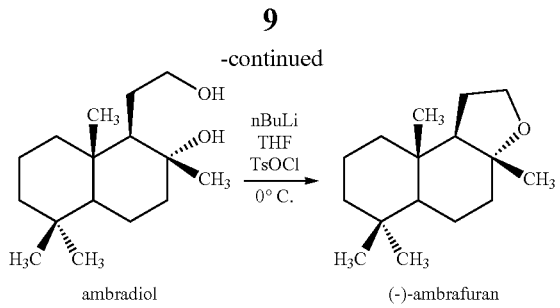

Chemical syntheses also imply the use of harsh conditions for certain steps (corrosive compounds, low temperature, toxic and dangerous reactants) that would be preferably avoided. Also, the use of organic solvents in chemical syntheses presents several drawbacks such as: drying costs, potential toxicity for consumers of solvent residues in the final product, lack of solvent selectivity resulting in the presence of unwanted compounds in the final product. Another concern with chemical syntheses of ambrafuran is that they generally result into racemic mixtures instead of isolated enantiomers. Moreover, consumers are more and more asking for "green products" obtained by environmentally friendly processes compatible with sustainable growth. One of the objectives of sustainable growth consists in avoiding the use of chemical reagents and the rejection of residual salts in the environment, which is incompatible with conventional syntheses of ambrafuran.

An alternative to chemical hemi-synthesis of ambrafuran from sclareol consists in replacing the first six or seven steps of the traditional transformation process leading respectively to sclareolide and to ambradiol intermediates with a biological conversion step.

The biological conversion of sclareol to sclareolide and ambradiol was first reported in U.S. Pat. No. 4,798,799 for the synthesis of ambradiol and in U.S. Pat. No. 4,970,163 for the synthesis of sclareolide and ambradiol.

The biological conversion of sclareol to sclareolide described in U.S. Pat. No. 4,970,163 uses the microorganisms *Cryptococcus albidus* saito, *skinner* var. *albidus*, ATCC 20918 or *Cryptococcus albidus*, ATCC 20921. Such biotransformation is carried out under aerobic conditions, in an aqueous nutrient medium containing sclareol. Further isolation and purification of sclareolide may be achieved by conventional techniques such as filtration or centrifugation, by solvent extraction, distillation or crystallization. A method for purifying sclareolide is reported in U.S. Pat. No. 5,945,546. Once extracted and purified from the fermentation broth, sclareolide may then be converted into ambradiol by hydrogenation as reported in the eight-step chemical synthesis.

The biological conversion of sclareol to ambradiol is described in U.S. Pat. No. 4,798,799 using the microorganism *Hyphozyma roseoniger* (CBS214.83 and ATCC 20624) and in U.S. Pat. No. 4,970,163 using the microorganisms Bensingtonia Ciliata ATCC 20919 or *Cryptococcus Laurentii* ATCC 20920. Such biotransformations are carried out under aerobic conditions at 20° C., in an aqueous nutrient medium containing sclareol.

In U.S. Pat. No. 4,798,799, ambradiol is then dehydrated to give ambrafuran directly from the aqueous nutrient medium or after recovery. More specifically, recovery and purification of ambradiol may be achieved by conventional techniques such as filtration or centrifugation, by solvent extraction, distillation or crystallization. Especially, ambradiol may be extracted with ethyl acetate and crystallized from hexane/chloroform.

The conversion of ambradiol to (−)-ambrafuran may then be performed by conventional cyclization methods, such as by reacting ambradiol with toluene-p-sulfonylchloride in pyridine at 0° C., followed by solvent extraction. Alternatively, dehydration is achieved in the presence of an acid catalyst, most often in the form of a strong mineral acid, heteropolyacids, sulfonic acids or DMSO. One of the drawbacks of such methods is that in acidic conditions, ambrafuran is likely to isomerize readily to the more thermodynamically stable, but olfactively much weaker iso-ambrafuran. Also, such methods do not solve the problems associated with chemical synthesis as they also contribute to undesired environmental and economic burdens through the rejection of waste salts, the need to regenerate the catalyst or the use of organic petrochemical solvents.

As already mentioned above, patent application US2010/0248316 proposes an alternative cyclization method consisting in exposing ambradiol to an activated zeolite (scheme 4). This method allows the dehydration of the diol into (−)-ambrafuran, ambradiol being obtained by the biological conversion disclosed in U.S. Pat. No. 4,798,799. Therefore, starting from racemic natural sclareol, this enantioselective method achieves the production of a single enantiomer of ambrafuran in two steps.

Scheme 4

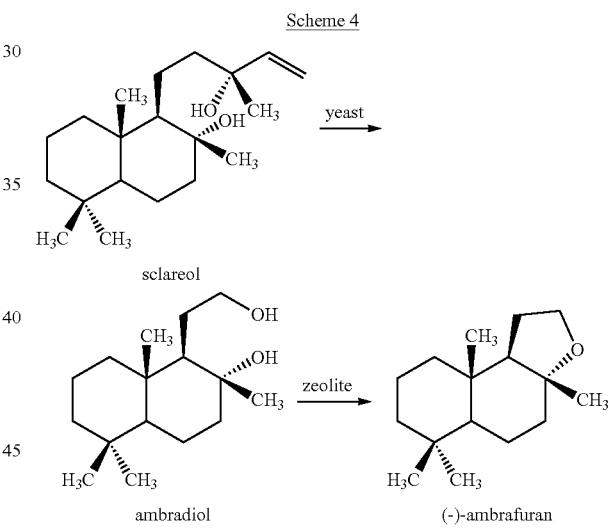

In patent application US2010/0248316, the dehydration of ambradiol on an activated zeolite is carried out in hexane or in toluene at room temperature or in dimethylsulfoxyde or ethyl acetate, optionally heating the solution. At the end of the reaction, solvent should be removed under reduced pressure.

Contrary to other dehydrations that need controlled temperatures, patent application US2010/0248316 discloses a total conversion at room temperature, generally in less than two hours.

Despite advantages of the method disclosed in US2010/0248316 such as the suppression of toxic reactants, several drawbacks remain that were detailed in part A above, the main ones being:

the use of specific organic solvents to extract and purify ambradiol from the fermentation broth, to carry out the dehydration reaction and to extract and purify (−)-ambrafuran;

the restrictive activation step of the zeolite.

B.2. Use of the Process of the Invention for Manufacturing of Ambrafuran

Therefore, there is a need for an improved process for the production of products of interest selected from the group comprising sclareolide, ambradiol and/or ambrafuran from sclareol presenting the following characteristics:

avoiding the use of synthetic solvents or organic solvents of petrochemical origin at any step of the transformation process, in particular during purification or transformation steps, and/or avoiding the use of chemical reactants that result in the production of salts and other potentially toxic or polluting spent material, and/or using a continuous process to reduce the time of transformation and number of steps involved, and/or simplifying the conditions of purification and/or conversion of sclareol, sclareolide and ambradiol leading to the production of (−)-ambrafuran.

The Applicant found that the stereoselective cyclodehydration process of the present invention may be incorporated into an integrated manufacturing process of ambrafuran without the use of petrochemical organic solvents or chemical reactants. Especially, the Applicant showed that ambradiol may be converted into (−)-ambrafuran of high purity through the process of the invention.

Moreover, in this invention, the Applicant identified a complete process for manufacturing ambrafuran from sclareol comprising an initial biological conversion of sclareol and at least one further step performed according to the cyclo-dehydration process of the present invention.

Given that the biological conversion of sclareol may provide ambradiol and/or sclareolide, the invention also relates to the purification of sclareolide and/or ambradiol from a bioconversion broth.

Therefore, the Applicant showed that sclareolide and/or ambradiol may be efficiently purified from a bioconversion broth using supercritical $CO_2$ with or without other cosolvents such as ethanol or methanol.

These elements were not foreseeable and required experimental work to be established.

B.3. Supercritical Conditions Applied to Ambradiol and/or Sclareolide Purification The Applicant carried out research for applying supercritical fluids to the, purification of sclareolide and/or ambradiol from a bioconversion broth and, surprisingly, showed that sclareolide and ambradiol may be efficiently separated from a bioconversion broth using supercritical $CO_2$ with or without cosolvent.

Generally, the ability to extract and purify substances using supercritical $CO_2$ is difficult to predict without experimentation. The efficiency of supercritical extraction and purification depends altogether on the characteristics of the targeted substance such as polarity and molecular mass, on the temperature and pressure parameters of the supercritical fluid, but also on the characteristics of the medium containing the substances to be extracted, such as composition, polarity, granularity, etc. In weak solubility or affinity conditions, the addition of a cosolvent such as methanol or ethanol is often necessary but may result in lower selectivity. Therefore, the ability to extract substances in high purity from a medium using supercritical fluids is to be explored on a case-by-case basis and conditions of pressure and temperature have to be optimized for each substance or mix thereof.

Whether or not sclareolide and mostly ambradiol were soluble in supercritical carbon dioxide with or without cosolvent and whether the selectivity of their extraction from a bioconversion broth was acceptable in regard of the overall production process was therefore not foreseeable; to the contrary, in view of the polarity brought by the two hydroxyl functions in ambradiol and of the presence of oxygen atoms in sclareolide, the skilled artisan was induced to estimate that solubility of these compounds in supercritical carbon dioxide was mostly questionable. For example, initial experiments in dry form revealed very poor solubility of both compounds in pure supercritical $CO_2$ whereas solubility of ambradiol in pure supercritical $CO_2$ proved to be enhanced when extraction was performed from an aqueous medium such as a bioconversion broth.

B.4. Evaluation of the Feasibility of Supercritical Purification of Sclareolide and Ambradiol from Bioconversion Broth Furthermore, the ability to extract sclareolide or ambradiol in high purity from a bioconversion broth required practical experimentation in order to test the relative affinity of the targeted substances for supercritical $CO_2$ with and without cosolvent versus their aqueous medium or the potential pollution of the supercritical extracts by additives contained in the bioconversion broth such as growth factors, nutrients, substrates or by-products produced by the organisms or biocatalysts.

Tests were therefore carried out by the Applicant and it was found that the extraction of sclareolide or ambradiol by supercritical $CO_2$ with and without cosolvent from the aqueous medium used for the biological conversion was possible in high purity, even in the presence of several additives such as growth factors, nutrients and substrates, all of which could have retained ambradiol or sclareolide within the broth or polluted the extract.

The Applicant further found that several of the compounds used in yeast nutrient mediums or as co-factors in the case of biocatalysis are not soluble in supercritical $CO_2$ with and without cosolvent and/or that their affinity for the supercritical solvent mixture did not allow their efficient extraction from the bioconversion broth. Some of the bioconversion broth additives identified by the Applicant in regard of the existing art include without being limited to: enzymes, carbon sources such as glucose, galactose, L-sorbose, maltose, sucrose, cellobiose, trehalose, L-arabinose, L-rhamnose, ethanol, glycerol, L-erythrithol, D-mannitol, lactose, melibiose, raffinose, melezitose, starch, D-xylose, D-sorbitol, a-methyl-D-glucoside, lactic acid, citric acid, succinic acid; organic sources of nitrogen such as peptone, meat extract, yeast extract, corn steep liquor, casein, urea, amino acids but preferably inorganic sources of nitrogen such as: nitrates, nitrites, inorganic ammonium salts; inorganic salts such as phosphates of magnesium, potassium, calcium or sodium; several vitamins but preferably vitamin B1, B2, B3, B5, B6, B7, B9, B12; minerals such as Fe, Mo, Cu, Mn and B as well as most acids, preferably inorganic acids, used to adjust broth pH. In general, the Applicant found that such additives showed poor solubility in supercritical $CO_2$ with or without cosolvent at the operating conditions used for the extraction of sclareolide and/or ambradiol.

Therefore, the Applicant established that ambradiol and/or sclareolide may be purified from a bioconversion broth with up to 99% purity and 100% yield, using one or two steps of supercritical $CO_2$ extraction.

When sclareolide is produced, transformation into ambradiol may then be performed by methods known to the art, such as by using metal hydrides such as $LiAlH_4$ or RedAl®.

B.5. Evaluation of the Feasibility of the Synthesis of Ambrafuran in HTW

The Applicant also investigated, as shown in FIG. 4, the feasibility of the conversion of ambradiol into ambrafuran using HTW.

Ambradiol is non-miscible with and non-soluble in water or HTW up to around 250° C., at which point ambradiol is degraded by HTW. At the same time, ambradiol also bears a chiral tertiary alcohol which is likely to lose its chirality during acid-catalyzed dehydration. Therefore, ambradiol conforms with both definitions of a Chiral Diol and a Non-Soluble Diol.

The use of HTW conditions was never envisaged for the synthesis of ambrafuran from ambradiol. Indeed, catalytic mechanisms are difficult to predict and the sensitivity of reactants and products might have prevented reaching the temperatures needed to operate cyclo-dehydration reactions in HTW.

The use of HTW altogether as a reaction medium, a solvent and a catalyst in dehydration transformations is documented in JOC Article "Kinetics and Mechanism of Tetrahydrofuran Synthesis via 1,4-Butanediol Dehydration in High-Temperature Water", where Hunter, Ehrenberger and Savage describe the dehydration of the diol 1,4-butanediol (BDO) to the furan tetrahydrofuran (THF) using sub-critical water (HTW) at temperatures between 200° C. and 350° C. However, according to Applicant's knowledge, no specific information can be found in prior art regarding the stereoselective transformation of ambradiol into (−)ambrafuran using HTW.

Due to the configuration of the ambradiol molecule, one skilled in the art, in view of the above article, may conclude that using HTW on ambradiol could lead to numerous possible transformations. Also, at ambient temperature, BDO and THF are liquids miscible with water, whereas ambradiol consists of a white solid that melts around 132° C. while remaining immiscible with water in HTW. No indication was found in the prior art as regards the ability of ambradiol to form a unique phase with HTW, the impact of HTW on such a molecule at a given temperature as well as the very stability of such a molecule at the temperatures potentially leading to the envisaged transformations.

The Applicant however carried tests using a pressure-controlled vessel containing HTW and noticed that ambradiol could be dehydrated into (−)ambrafuran, the primary isomeric conformation of interest, in high yield and, more surprisingly, with a purity up to about 92.5% using HTW, preferably mixed with a supercritical fluid and/or gas such as $CO_2$ and/or $N_2$ and/or other additives, preferably while stirring such mixture between 10 and 1500 rpm and/or while homogenizing the mixture with methods known to the art such as ultrasonication or homogenization.

B.6. Evaluation of the Synthesis of Ambrafuran Using a Solid Catalyst Such as for Example Montmorillonite Clays in Water The Applicant also investigated, as shown in FIG. 3, the feasibility of the conversion of ambradiol into ambrafuran using a solid catalyst such as for example K-type montmorillonite clays in water.

Given that ambradiol is a Non-Soluble and Chiral Diol, water had never been used as a solvent for performing such a transformation. Moreover, U.S. Pat. No. 5,670,670 requires specifically that water content should remain below 2% when performing the cyclodehydration of ambradiol using montmorillonite clays.

Surprisingly, the Applicant found that ambradiol could be efficiently cyclo-dehydrated into (−)ambrafuran with a purity above 90% using a solid catalyst such as for example K-type montmorillonite clays, preferably when the reaction mixture had a water content above 3% and, more generally, above 80%, between room temperature and 90° C.

Furthermore, when combining a solid catalyst such as for example montmorillonite clays and HTW conditions, the Applicant found that (−)ambrafuran could be produced from ambradiol at close to 98% yield and in above 95% purity in less than 15 minutes by using preferably montmorillonite clays when the reaction mixture had a water content above 3% and, more generally, above 80% and while subjecting further the reaction mixture to HTW conditions.

Therefore, the Applicant identified a transformation process that can not only achieve the purification of sclareolide and/or ambradiol from a bioconversion broth but also the chemical cyclodehydration of ambradiol into (−)-ambrafuran.

The Applicant found that not only supercritical conditions were useful for the purification of intermediate compounds, i.e. sclareolide and/or ambradiol, but also that HTW conditions and/or a solid catalyst such as for example K-type montmorillonites with high water content could be used for the chemical conversion of ambradiol into (−)-ambrafuran. These elements are summarized in FIG. 1.

SUMMARY

The present invention relates to a process for the manufacturing of a cycloether derivative comprising
(i) the stereoselective cyclodehydration in water of 1,4- or 1,5-diols comprising at least one chiral tertiary alcohol functional group with retention of the initial chirality, and/or
(ii) the cyclodehydration in water of 1,4- or 1,5-diols, said diols being non-miscible with and/or non-soluble in water),
into corresponding cycloether derivatives,
by bringing the reaction mixture to high temperature water (HTW) conditions and/or by mixing the aqueous reaction mixture with a solid catalyst.

According to one embodiment, the process of the invention is a for the manufacturing of a cycloether derivative of general formula (IIa) or (IIb)

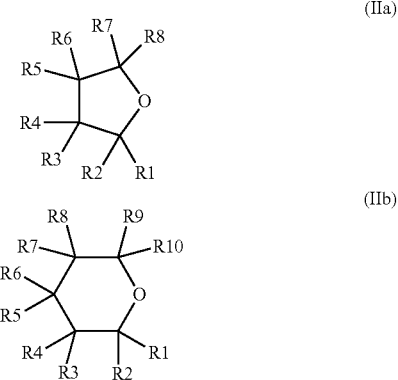

wherein R1 and R2 are the same or different and are selected from optionally substituted groups selected from alkyl, alkenyl, alkynyl, cycloalkyl, cycloalkenyl, aryl, an heterocyclic group, or form a substituted or unsubstituted ring with R3 or R4, or form together a substituted or unsubstituted ring, R3 and R4 are the same or different and are an hydrogen atom or selected from optionally substituted groups selected from alkyl, alkenyl, alkynyl, cycloalkyl, cycloalkenyl, aryl, an heterocyclic group, or form a substituted or unsubstituted ring with R1 or R2 and/or with R5 or R6, or form together a substituted or unsubstituted ring, R5 and R6 are the same or different and are an hydrogen atom or selected from optionally substituted groups selected from alkyl, alkenyl, alkynyl, cycloalkyl, cycloalkenyl, aryl, an heterocyclic group, or form a substituted or unsubstituted ring with R3 or R4 and/or with R7 or R8 when applicable, or form together a substituted or unsubstituted ring, R7 and R8 are the same or different and are an hydrogen atom or selected from optionally substituted groups selected from alkyl, alkenyl, alkynyl, cycloalkyl, cycloalkenyl, aryl, an heterocyclic group, or form a substituted or unsubstituted ring with R5 or R6 and/or with R9 or R10 when applicable, or form together a substituted or unsubstituted ring, R9 and R10 are the same or different and are an hydrogen atom or selected from optionally substituted groups selected from alkyl, alkenyl, alkynyl, cycloalkyl, cycloalkenyl, aryl, an heterocyclic group, or form a substituted or unsubstituted ring with R7 or R8, or form together a substituted or unsubstituted ring.

comprising the cyclodehydration of respectively a 1,4- or 1,5-diol of general formula (Ia) or (Ib)

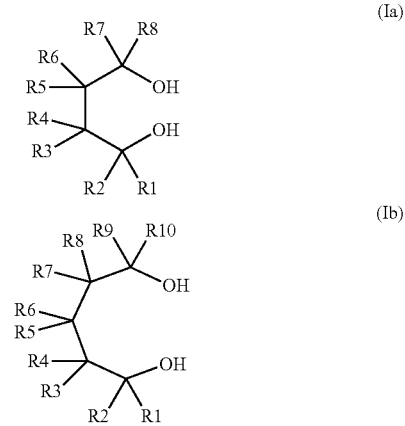

wherein R1, R2, R3, R4, R5, R6, R7, R8, R9 and R10 are as described above.

According to an embodiment, R1 and R2 are different, the corresponding alcohol functional group being a chiral tertiary alcohol functional group.

According to an embodiment, the solid catalyst is a montmorillonite, preferably a K-type montmorillonite.

The invention further relates to a device for implementing the process of the invention, comprising a pressured vessel which may be packed with a solid catalyst, such as for example montmorillonite, the pressured vessel being preferably associated with a heating device capable of heating the walls of the vessel.

According to an embodiment, the 1,4-diol is ambradiol and wherein the cycloether derivative is ambrafuran, preferably (−)-ambrafuran.

According to an embodiment, the process further comprises a preliminary step of biological conversion of sclareol into ambradiol.

According to an embodiment, ambradiol is purified using supercritical extraction.

According to an embodiment, the process further comprises a preliminary step of biological conversion of sclareol into sclareolide.

According to an embodiment, sclareolide is purified using supercritical extraction.

According to an embodiment, the process is continuous or semi-continuous.

According to an embodiment, the step of biological conversion, sclareol is contacted with a microorganism capable of converting it into sclareolide or ambradiol, said microorganism being in an aqueous nutrient medium.

According to an embodiment, the microorganism is selected from the group comprising *Cryptococcus albidus* saito, *skinner* var. *albidus*, ATCC 20918 or *Cryptococcus albidus*, ATCC 20921, and is capable to convert sclareol into sclareolide.

According to an embodiment, the microorganism is selected from the group comprising *Hyphozyma roseoniger* (CBS214.83 and ATCC 20624) and is capable to convert sclareol into ambradiol.

DEFINITIONS

In the present invention, the following terms have the following meanings:

"about" preceding a figure means plus or less 10% of the value of said figure.

"alkenyl" refers to any linear or branched hydrocarbon chain having at least one double bond, of 2 to 12 carbon atoms, and preferably 2 to 6 carbon atoms.

"alkyl" refers to any saturated linear or branched hydrocarbon chain, with 1 to 12 carbon atoms, preferably 1 to 6 carbon atoms, and more preferably methyl, ethyl, propyl, isopropyl, n-butyl, sec-butyl, isobutyl and tert-butyl.

"alkynyl" refers to any linear or branched hydrocarbon chain having at least one triple bond, of 2 to 12 carbon atoms, and preferably 2 to 6 carbon atoms.

"aryl" refers to a mono- or polycyclic system of 5 to 20, and preferably 6 to 12, carbon atoms having one or more aromatic rings (when there are two rings, it is called a biaryl) among which it is possible to cite the phenyl group, the biphenyl group, the 1-naphthyl group, the 2-naphthyl group, the tetrahydronaphthyl group, the indanyl group and the binaphthyl group. The term aryl also means any aromatic ring including at least one heteroatom chosen from an oxygen, nitrogen or sulfur atom. The aryl group can be substituted by 1 to 3 substituents chosen independently of one another, among a hydroxyl group, a linear or branched alkyl group comprising 1, 2, 3, 4, 5 or 6 carbon atoms, in particular methyl, ethyl, propyl, butyl, an alkoxy group or a halogen atom, in particular bromine, chlorine and iodine.

"biological conversion" refers to the transformation of organic compounds, usually in aqueous or polar medium such as water or ionic liquids, using microorganisms such as yeast, funghi or bacteria or using enzymatic treatment.

"bioconversion broth" refers to the medium used to perform a biological conversion together with the substrate, microorganisms, enzymes as well as additives such as yeast growth factors, sugars, surfactants and co-factors.

"Chiral Diols" refers to 1,4- or 1,5-diols comprising at least one chiral tertiary alcohol functional group. Preferably, Chiral Diols of the invention comprise a chiral tertiary alcohol functional group and a primary alcohol functional group.

"cyclodehydration" refers to the removal of a molecule of water from a substance, leading to the cyclization of said substance.

"continuous" refers to a transformation process whereby production can be performed with no interruption assuming a constant supply to the process of the components necessary for the production, such as substrate to be transformed, power or catalysts. Continuous can also be defined in contrast to batch processes where only a fixed amount of product can be processed at a time, usually in vessels or containers, before some of the elements necessary to the process need to be reloaded, recharged or exchanged through process interruption.

"cycloalkenyl" refers to a substituted or unsubstituted cyclic alkenyl group.

"cycloalkyl" refers to a substituted or unsubstituted cyclic alkyl group, preferably cyclopropyl, cyclopentyl or cyclohexyl.

"dehydration" refers to the removal of a molecule of water from a substance. The transformation of ambradiol to (−)-ambrafuran will fall within this definition.

"heterocyclic group" refers to a cyclic group such as cycloakyl or cycloalkenyl comprising an heteroatom chosen from oxygen, nitrogen or sulfur atom.

"hydrogenation", for the purpose of this paper, consists of the addition of hydrogen atoms to a molecule and will also include reactions of reduction. The transformation of sclareolide into ambradiol will fall within this definition.

"Non-Soluble Diols" refers to 1,4- or 1,5-diols non-miscible with and/or non-soluble in water or HTW at operating conditions. Preferably, Non-Soluble Diols of the invention comprise a tertiary alcohol functional group and a primary alcohol functional group.

"Non-Soluble Chiral Diols" refers to 1,4- or 1,5-diols comprising at least one chiral tertiary alcohol functional group, non-miscible with and/or non-soluble in water or HTW at operating conditions. Preferably, Non-Soluble Chiral Diols of the invention comprise a chiral tertiary alcohol functional group and a primary alcohol functional group "purification" refers to the action of isolating a chosen compound usually from one or several compounds. For the purpose of this paper, "purification" will include the action generally referred to as "extraction" and consisting of the initial isolation of a compound or mix of compounds containing the targeted compound from a raw material, which can be for example a plant or a bioconversion broth.

"subcritical water=high-temperature water (HTW)" refers to water at temperatures ranging from 80° C. to 380° C., preferably from 100° C. to 350° C. and at pressures ranging from 0.001 bar to 350 bar, provided that for any given temperature, pressure is chosen no lower than the minimum level required to maintain water below its boiling point.

"substituted or unsubstituted ring" refers to cycloakyl, cycloalkenyl, heterocyclic, aryl group.

"supercritical extraction" refers to the action of extracting a substance from a mix of substances by contacting such mix with a supercritical fluid in a pressured vessel (the extractor) so as to dissolve selectively the targeted substance in the supercritical fluid. The charged supercritical fluid is then transferred to another vessel (the separator) where it is expanded to it gaseous form, thereby isolating the targeted compound.

"supercritical fluid" refers to a fluid at temperatures and pressures near or above its supercritical point.

"supercritical $CO_2$" refers to $CO_2$ potentially mixed with a cosolvent such as ethanol at temperatures above 30.95° C. and pressures above 73.8 bar.

DETAILED DESCRIPTION

Figure 1:
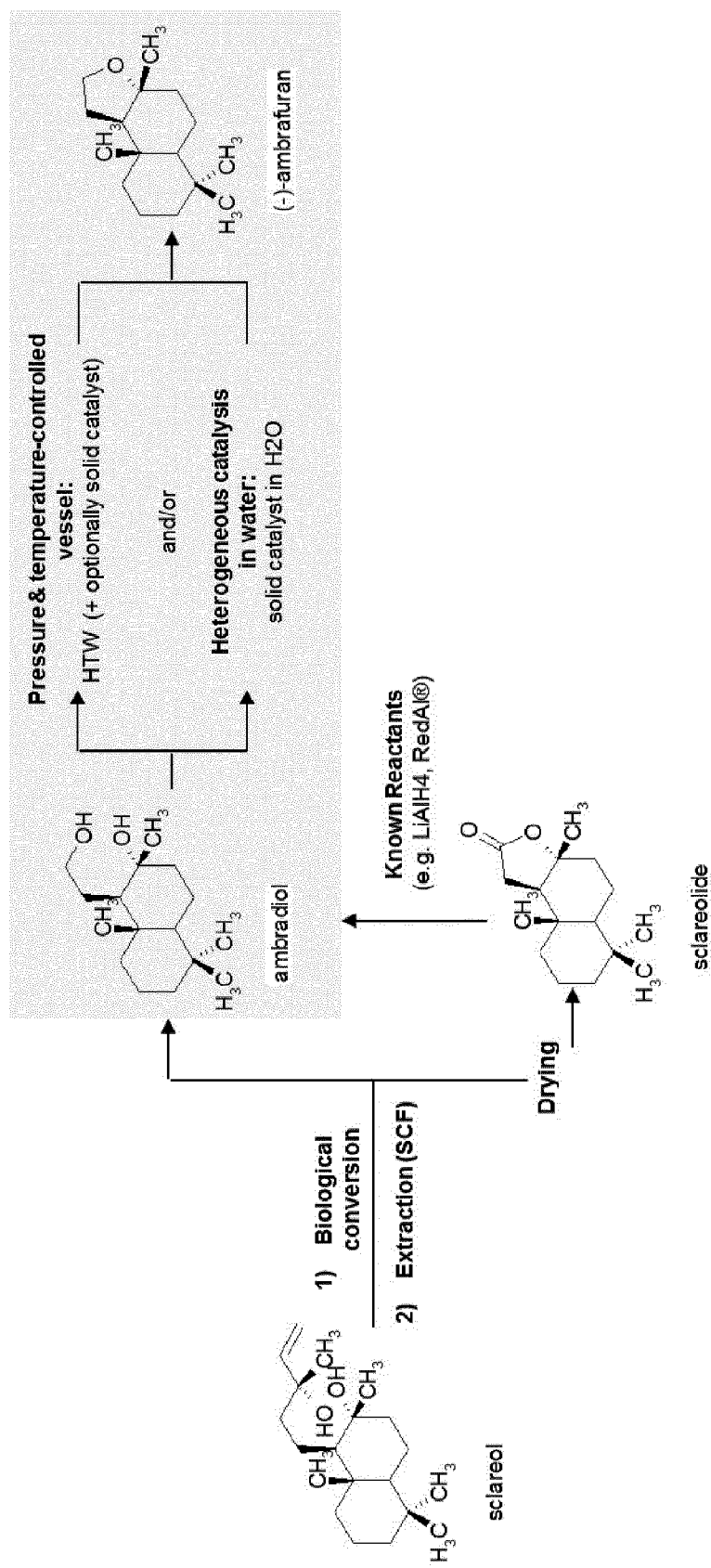
FIG. 1 is a scheme showing different routes of synthesis of sclareolide, ambradiol and (−)-ambrafuran with sclareol as starting product.

I. Manufacturing of Chiral Cycloether Derivatives
I.1. Process for Enantioselective Cyclodehydration The present invention relates to a process for manufacturing tetrahydrofuran, tetrahydropyran and, more generally, cycloether derivatives through the cyclodehydration of 1,4- or 1,5-diols. More specifically, the process of the invention involves (i) the stereoselective cyclodehydration in water of Chiral Diols with retention of the initial chirality and/or (ii) the cyclodehydration in water of Non-Soluble Diols, in both cases into corresponding cycloether derivatives, by bringing the reaction mixture to high temperature water (HTW) conditions and/or by mixing the aqueous reaction mixture with a solid catalyst, such as for example a K-type montmorillonite.

According to one embodiment, the process of the present invention comprises the cyclodehydration of Chiral Diols of general formulae (Ia') or (Ib') to give the corresponding cycloether derivative of respective formulae (IIa') and (IIb') wherein the chiral configuration of the carbon atom bearing R1 and R2 is retained:

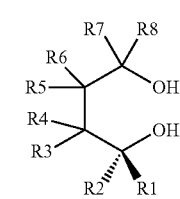 (Ia')

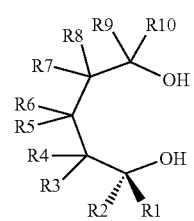 (Ib')

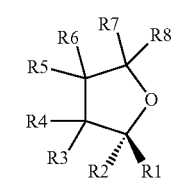 (IIa')

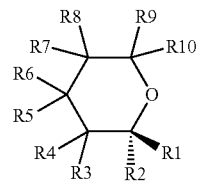 (IIb')

wherein R1 and R2 are the same or different and are selected from optionally substituted groups selected from alkyl, alkenyl, alkynyl, cycloalkyl, cycloalkenyl, aryl, an heterocyclic group, or form a substituted or unsubstituted ring with R3 or R4, or form together a substituted or unsubstituted ring, R3 and R4 are the same or different and are an hydrogen atom or selected from optionally substituted groups selected from alkyl, alkenyl, alkynyl, cycloalkyl, cycloalkenyl, aryl, an heterocyclic group, or form a substituted or unsubstituted ring with R1 or R2 and/or with R5 or R6, or form together a substituted or unsubstituted ring, R5 and R6 are the same or different and are an hydrogen atom or selected from optionally substituted groups selected from alkyl, alkenyl, alkynyl, cycloalkyl, cycloalkenyl, aryl, an heterocyclic group, or form a substituted or unsubstituted ring with R3 or R4 and/or with R7 or R8 when applicable, or form together a substituted or unsubstituted ring, R7 and R8 are the same or different and are an hydrogen atom or selected from optionally substituted groups selected from alkyl, alkenyl, alkynyl, cycloalkyl, cycloalkenyl, aryl, an heterocyclic group, or form a substituted or unsubstituted ring with R5 or R6 and/or with R9 or R10 when applicable, or form together a substituted or unsubstituted ring, R9 and R10 are the same or different and are an hydrogen atom or selected from optionally substituted groups selected from alkyl, alkenyl, alkynyl, cycloalkyl, cycloalkenyl, aryl, an heterocyclic group, or form a substituted or unsubstituted ring with R7 or R8, or form together a substituted or unsubstituted ring.

According to one embodiment, the process of the present invention comprises the cyclodehydration of Non-Soluble Diols of general formulae respectively (Ia) and (Ib) to give the corresponding cycloether derivative of respective formulae (IIa) and (IIb):

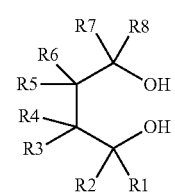 (Ia)

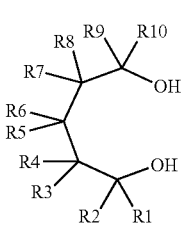 (Ib)

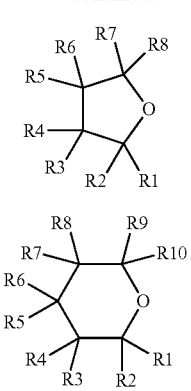

(IIa)

(IIb)

wherein R1, R2, R3, R4, R5, R6, R7, R8, R9 and R10 are as described above.

According to one embodiment, the process of the present invention comprises the cyclodehydration of Chiral Diols that are also Non-Soluble Diols of general formulae respectively (Ia') and (Ib') to give the corresponding cycloether derivative of respective formulae (IIa') and (IIb') wherein the chiral configuration of the carbon atom bearing R1 and R2 is retained:

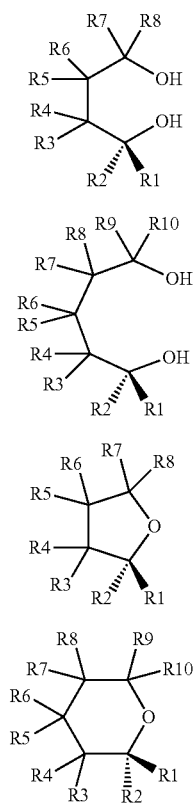

(Ia')

(Ib')

(IIa')

(IIb')

wherein R1, R2, R3, R4, R5, R6, R7, R8, R9 and R10 are as described above.

According to a specific embodiment the 1,4-diol cyclodehydrated in the process of the invention is ambradiol represented in Scheme 1. In this embodiment, the resulting product is (−)-ambrafuran.

I.2. Heterogeneous Catalysis Over a Solid Catalyst Such as for Example K-Type Montmorillonite Clays According to one embodiment, the process of the invention is performed in water at temperatures ranging from room temperature up to 80° C. In one embodiment, the temperature is higher than 25°, preferably between 40 and 80° C., more preferably but not necessarily above the Targeted Diol melting point.

According to one embodiment, the Targeted Diol is a Non-Soluble Diol. According to another embodiment the Targeted Diol is a Chiral Diol. According to another embodiment, the Targeted Diol is a Non-Soluble Chiral Diol.

In one embodiment, the Targeted Diol is mixed with a solid catalyst such as for example K-type montmorillonite clay and water in a vessel, preferably K10 montmorillonites.

In one embodiment, total water content of the reaction mixture is between 3% and 99.9%, preferably between 50% and 80%, more preferably between 60% and 70%.

In one embodiment, solvent and/or surfactants such as for example TWEEN80, THF or ether are added to the reaction mixture.

In one embodiment, solvent and/or surfactants such as for example TWEEN80, THF or ether are mixed with the Targeted Diol prior to its incorporation into the reaction mixture.

In one embodiment, the reaction mixture is mixed or homogenized using methods known to the art, preferably using ultrasonication.

One advantage of cyclodehydration in water using a soli catalyst such as preferably montmorillonite clay is that there is no need for consumable chemicals other than water, the reaction can be run without the use of an organic solvent even in the case of Non-Soluble Diols and product separation can be performed easily, especially in the case of Non-Soluble Diols.

In one embodiment, the reaction is allowed to run for between 1 hour and 72 hours, preferable between 15 and 24 hours.

In another embodiment, the solid catalyst, preferably montmorillonite catalyst, is reused following the cyclization reaction.

In another embodiment, the cycloether derivative is removed from the reaction mixture by filtration, decanting, centrifugation, supercritical fluid extraction or solvent extraction but preferably using a supercritical fluid.

I.3. High-Temperature Water (HTW) Conditions, Potentially Combined with a Solid Catalyst Such as for Example Montmorillonite Clays According to one embodiment, the process of the invention is performed in HTW at HTW temperature and pressure conditions. In one embodiment, the temperature is higher than 80° C., preferably is ranging from 110° C. to 200° C., preferably from 130 to 170° C. In one embodiment, the pressure is ranging from 0.001 to 350 bars, preferably from 0.1 to 70 bars, more preferably from 1.5 to 15 bars. In another embodiment, the pressure is ranging from 1 to 30 bars, preferably from 2 to 10 bars, more preferably is about 5 bars.

According to one embodiment, the Targeted Diol is a Non-Soluble Diol. According to another embodiment the Targeted Diol is a Chiral Diol. According to another embodiment, the Targeted Diol is both a Non-Soluble Chiral Diol.

In one embodiment, water is brought to HTW conditions or close to HTW conditions in a pre-heating vessel prior to contacting the diol.

In one embodiment, prior to performing the cyclodehydration reaction, water is degassed using methods known to the art. In another embodiment, water is not degassed.

In one embodiment, $CO_2$ and/or $N_2$ and/or air or other gases or fluids and/or a cosolvent such as ethanol or tetrahydrofuran is/are added to the reaction mixture.

In one embodiment, the reaction mixture is mixed or homogenized using methods known to the art, preferably using ultrasonication. In one embodiment, such mixing is achieved using a static mixer.

In one embodiment, solvent and/or surfactants such as for example TWEEN80, THF or ether are added to the reaction mixture.

In one embodiment, solvent and/or surfactants such as for example TWEEN80, THF or ether are mixed with the Targeted Diol prior to its incorporation into the reaction mixture.

In one embodiment, the Targeted Diol is heated until its melting point prior to being added to HTW.

In one embodiment, $CO_2$ and/or $N_2$ are under supercritical conditions thereby forming an expanded liquid with the Targeted Diol.

In one embodiment, additives such as for example Lewis or Bronsted acids are added to the reaction mixture.

According to one embodiment, cyclodehydration is performed in a vessel optionally packed with a solid acid catalyst such as for example silica or a zeolite or a K-type montmorillonite, preferably a K10 montmorillonite.

In one embodiment, when K-type montmorillonites are added to the reaction mixture, total water content of the reaction mixture is between 3% and 99.9%, preferably between 50% and 80%, more preferably between 60% and 70%.

In another embodiment, the solid catalyst, preferably montmorillonite catalyst, is reused following the cyclization reaction.

One advantage of cyclodehydration in HTW is that conditions are compatible with a continuous process, do not require the use of consumable chemicals other than water and product separation can be performed easily, especially in the case of Non-Soluble Diols.

In one embodiment, following cyclodehydration, the mixture exiting the HTW reactor comprising HTW and the resulting cycloether derivative, is transferred into a collection vessel before being extracted or separated by conventional means including centrifugation, drying or filtration but preferably using a supercritical fluid.

According to one embodiment, the cycloether-charged HTW contained in the collection vessel is transferred to a separator vessel where pressure is lowered, thereby causing the HTW to turn into steam. Steam can then be extracted from the vessel by conventional means, thereby leaving the cycloether derivative virtually free of water.

II. Application to the Manufacturing of (−)-Ambrafuran

According to a specific embodiment, the Targeted Diol cyclodehydrated in the process of the invention is ambradiol. In this embodiment, the resulting product is (−)-ambrafuran. In this embodiment, ambradiol falls within the definition of a Non-Soluble Chiral Diol.

In an embodiment, ambradiol is obtained from a starting material which is sclareol. In an embodiment, the process for manufacturing ambradiol from sclareol comprises a step of biological conversion, which includes transformations using microorganisms as well as enzymatic treatments, of sclareol. In one embodiment, ambradiol obtained by biological conversion of sclareol may be purified within a pressured vessel using supercritical extraction.

In a specific embodiment, the biological conversion of sclareol may provide sclareolide. In one embodiment, sclareolide obtained by biological conversion of sclareol may be purified within a pressured vessel using supercritical extraction.

The present invention thus further relates to a process for manufacturing and purifying ambradiol and/or sclareolide and/or ambrafuran from a starting material which is sclareol, said process implementing a step performed within a pressured vessel, which is preferably a step under supercritical conditions and another step performed under HTW conditions.

The present invention also relates to a process for manufacturing and purifying ambradiol and/or sclareolide and/or ambrafuran from a starting material which is sclareol, said process implementing a step performed within a pressured vessel, which is preferably a step under supercritical conditions and another step performed in water using solid catalyst such as for example a K-type montmorillonite.

According to an embodiment, the process for manufacturing ambradiol and/or sclareolide and/or ambrafuran does not use organic solvents and/or chemical reactants at any step.

According to an embodiment, the transformation steps of sclareol into (−)ambrafuran are performed in water medium.

The manufacturing of sclareolide, ambradiol and (−)-ambrafuran is represented on FIGS. 1 and 2 and may be detailed as follows:

In an embodiment, sclareolide and/or ambradiol are purified following the biological conversion step through one or several supercritical $CO_2$ extraction(s) with or without cosolvent, followed, whenever necessary, by a separation step to recover purified sclareolide or ambradiol from the supercritical fluid.

In an embodiment, the supercritical purification of ambradiol and/or sclareolide from the bioconversion broth is performed at a pressure of 74 to 350 bars and preferably at a pressure of 100 to 250 bars and at a temperature of 31 to 80° C. and preferably between 35° C. and 45° C.

In an embodiment, the conversion of sclareolide into ambradiol is performed using methods known to the art such as for example by using $LiAlH_4$.

In an embodiment, ambradiol is chemically transformed into (−)-ambrafuran through a dehydration step using HTW in a pressured vessel In an embodiment, ambradiol is chemically transformed into (−)-ambrafuran using a solid catalyst such as for example K-type montmorillonite clay in water.

In an embodiment, the supercritical purification of ambradiol and/or sclareolide from the bioconversion broth is performed using supercritical CO2, preferably with a cosolvent such as for example ethanol or methanol.

In an embodiment, the supercritical purification of (−)ambrafuran following the chemical transformation of ambradiol is performed by conventional means including centrifugation, drying, filtration or a supercritical fluid, preferably using a supercritical fluid.

Figure 2:
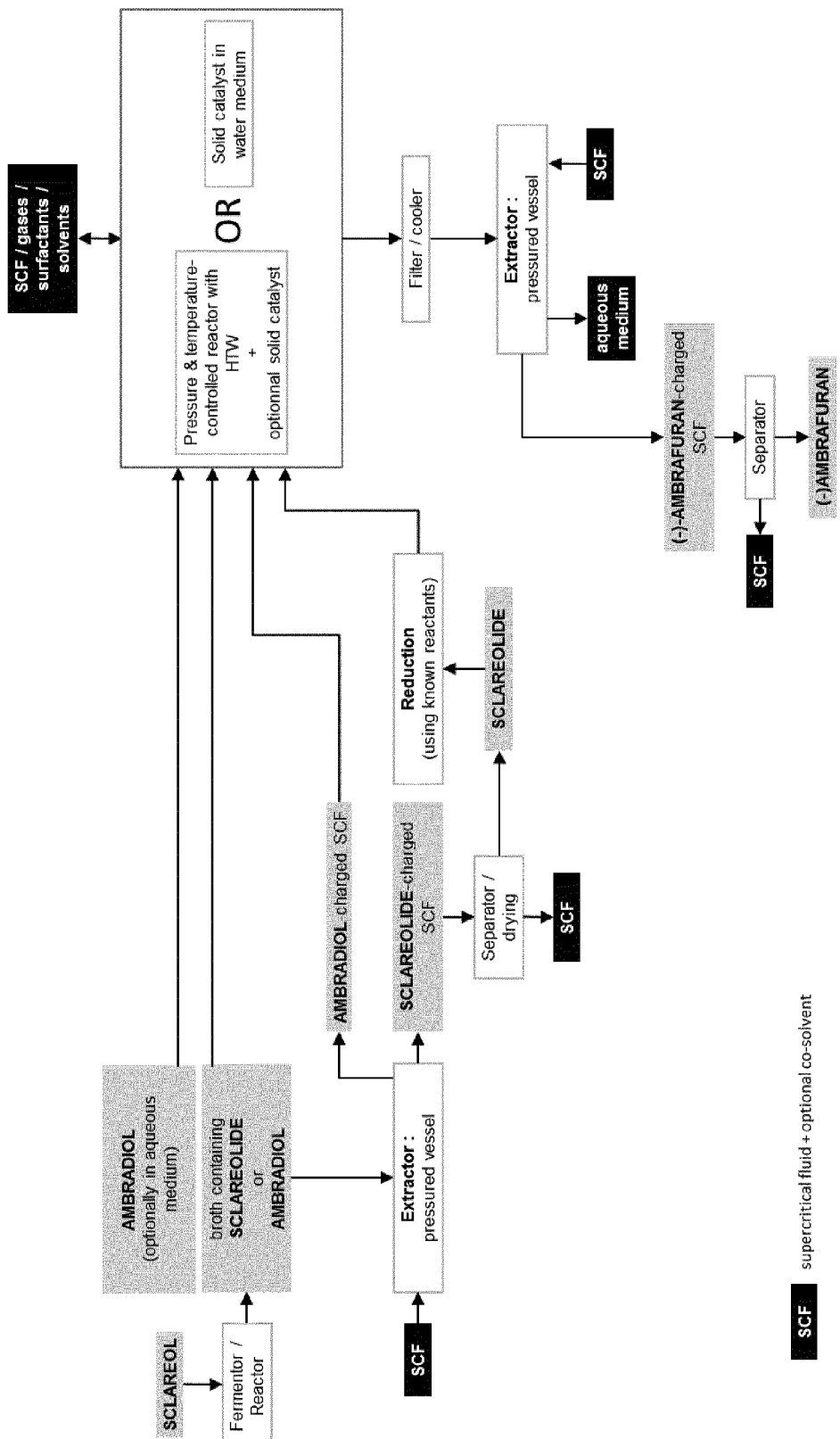
FIG. 2 is a scheme showing different routes of synthesis of sclareolide, ambradiol and (−)-ambrafuran comprising an enzymatic step and a further step of cyclodehydration.

The following detailed description of the process may be read with reference to FIG. 2.

II.1. Biological Conversion of Sclareol Leading to Sclareolide and/or Ambradiol

Figure 3:
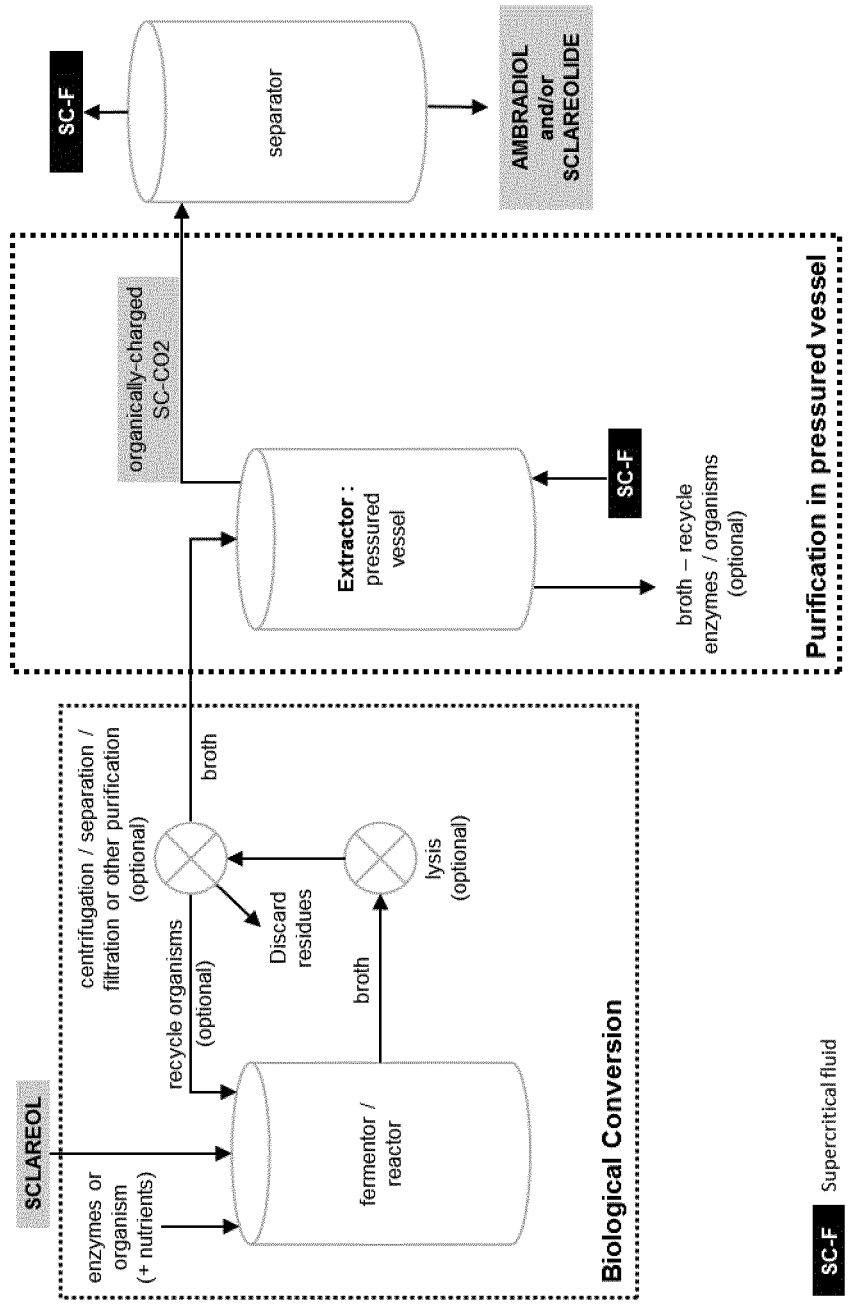
FIG. 3 is a scheme showing a process of synthesis of ambradiol and/or sclareolide comprising an enzymatic step and a further step of purification in a pressure-controlled vessel.
Figure 4:
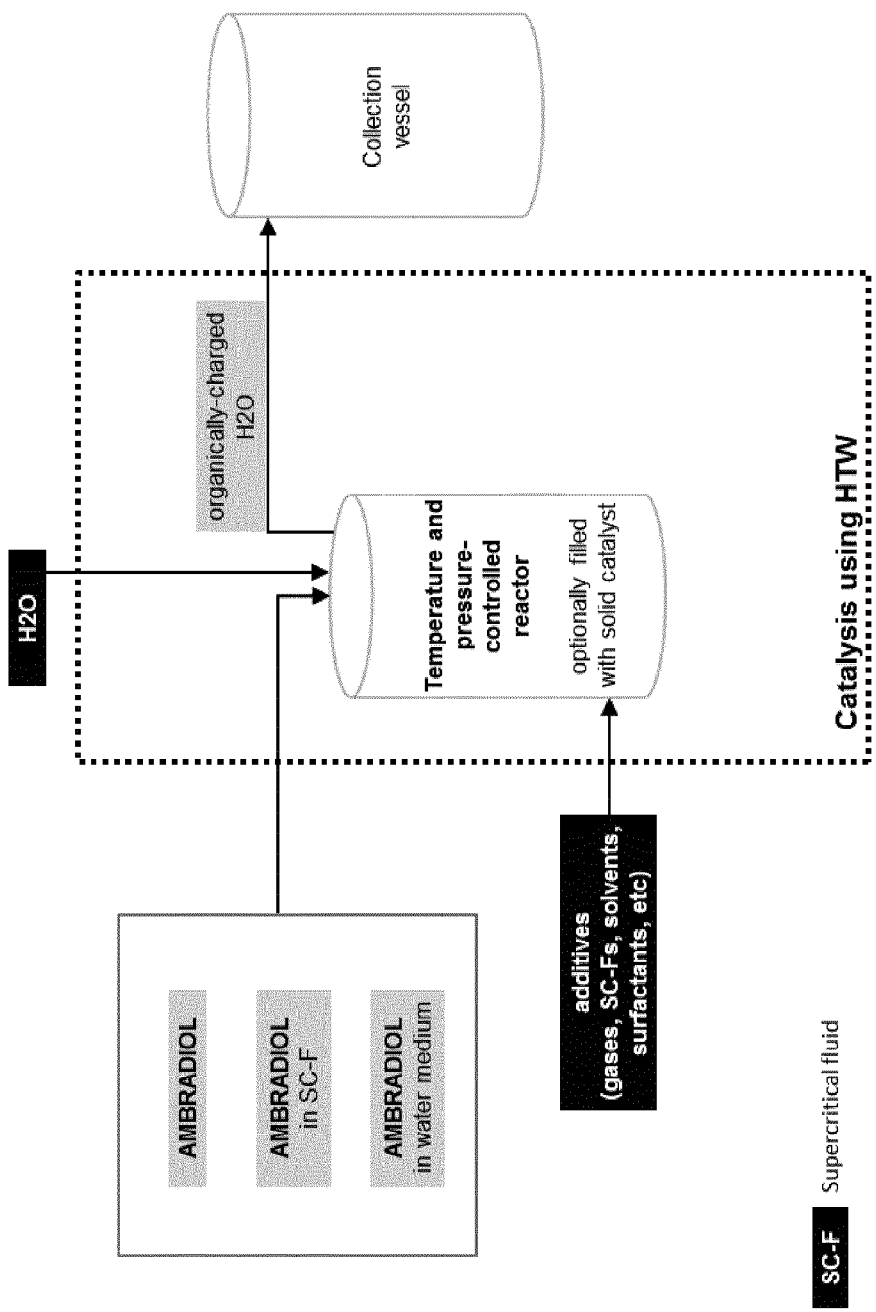
FIG. 4 is a scheme showing a process of synthesis of ambrafuran a cyclodehydration step using HTW.

As shown in FIG. 2, the first step is a biological conversion step. According to one embodiment, the biological conversion step using sclareol as a substrate and using a suitable microorganism or biocatalyst, generally within an aqueous nutrient medium, may produce sclareolide or ambradiol. A detailed view of the biological conversion is shown in FIG. 3, including possible recycling of yeast and/or other biocatalysts.

According to the invention, the biological conversion is performed with sclareol as a starting material whereby sclareol is contacted with biocatalysts such as for example enzymes and/or co-factors and/or a microorganism capable of converting it into sclareolide and/or ambradiol, said mixture being in an aqueous medium, and a further step performed within a pressured vessel to purify the sclareolide or ambradiol from such bioconversion broth.

In an embodiment, the microorganism is selected from the group comprising *Cryptococcus albidus* saito, *skinner* var. *albidus*, ATCC 20918 or *Cryptococcus albidus*, ATCC 20921, and is capable to convert sclareol into sclareolide. Then, sclareolide may be purified within a pressured vessel and recovered, or further transformed into ambradiol, which may be purified within a pressured vessel and recovered or further transformed into (−)-ambrafuran. Alternatively, sclareolide may be transformed directly into (−)-ambrafuran or a mixture of ambradiol and (−)-ambrafuran, which may be purified within a pressure vessel and recovered or further transformed into an even more pure (−)-ambrafuran.

In an alternative embodiment, the microorganism is selected from the group comprising *Hyphozyma roseoniger* (CBS214.83 and ATCC 20624), Bensingtonia Ciliata ATCC 20919 or *Cryptococcus Laurentii* ATCC 20920 and is capable to convert sclareol into ambradiol, which may be purified within a pressured vessel and recovered or transformed into (−)-ambrafuran.

In an alternative embodiment, the bioconversion broth contains enzymes derived from such microorganisms, possibly mixed with co-factors and other additives, solvents or surfactants known to the art.

In an embodiment, the fermentation broth resulting from the biological conversion step and containing sclareol and/or sclareolide and/or ambradiol is purified from the microorganisms. Said purification may be performed by means of centrifugation, filtration or separation techniques. This step of purification is a preliminary and optional step.

II.2. Purification Step in Pressured Vessel

The Applicant surprisingly found that sclareolide and ambradiol were soluble in supercritical $CO_2$ with or without the use of cosolvent at all of the operating conditions required for the purification of sclareolide and ambradiol.

Among extraction methods used in purification of products and performed within a pressured vessel, supercritical extraction presents several advantages that place it as a valuable alternative. This technique uses a supercritical fluid, which in certain conditions of pressure and temperature above critical point, may be considered as a solvent. Sometimes, the supercritical fluid is coupled with a cosolvent in order to adjust its polarity to that of the targeted compound(s). At the end of the extraction, the pressure is lowered and the state of the fluid converts from supercritical to gas, allowing its easy elimination from the extract.

According to another embodiment, as shown in FIG. 3, sclareolide and/or ambradiol is purified using a supercritical fluid to recover sclareolide or ambradiol in high purity.

According to a first embodiment, the supercritical fluid used in the supercritical extraction of the product of biological conversion of sclareol is supercritical carbon dioxide, preferably without but potentially with ethanol as a cosolvent.

According to one embodiment, the supercritical $CO_2$ extraction is carried at a temperature ranging from 31° C. to 90° C., but preferably between 31° C. and 45° C.

According to one embodiment, the supercritical $CO_2$ extraction is carried with a pressure ranging from 74 bars to 350 bars, preferably from 74 bars to 250 bars, preferably between 100 bars and 250 bars, preferably between 80 bars and 150 bars.

According to one embodiment, the yield of ambradiol or sclareolide after supercritical $CO_2$ extraction ranges from 85% to 99%.

According to one embodiment, the purity of sclareolide or ambradiol after supercritical $CO_2$ extraction ranges from 85% to 99%.

According to one embodiment, the recovered ambradiol and/or sclareolide is dried from residual water following extraction from the bioconversion broth. According to one embodiment, the recovered ambradiol is not dried from residual water following extraction from the bioconversion broth.

According to one embodiment, the recovered ambradiol and/or sclareolide may be subjected to another purification step using supercritical CO2 with or without cosolvent whereby potential remaining impurities may be finally removed.

The sclareolide-charged or ambradiol-charged supercritical $CO_2$ obtained at the end of the purification step may be passed in a separator vessel to recover purified sclareolide or ambradiol from the supercritical fluid following decompression or heating of the fluid to decrease its density and therefore release the organic substrate.

According to another embodiment, sclareolide-charged or ambradiol-charged supercritical $CO_2$ obtained at the end of the purification step is directly and continuously transferred to the next conversion step.

II.3. (−)Ambrafuran Production Using a Solid Catalyst Such as for Example K-Type Montmorillonite Clays According to one embodiment, the process of the invention is performed in water at temperatures ranging from room temperature up to 80° C. In one embodiment, the temperature is higher than 25°, preferably between 40 and 80° C.

In one embodiment, ambradiol is mixed with a solid catalyst such as for example K-type montmorillonite clay and water in a vessel, preferably K10 montmorillonites.

In one embodiment, total water content of the reaction mixture is ranging from 3% to 99.9%, preferably from 50% to 80%, more preferably from 60% to 70%.

In one embodiment, solvent and/or surfactants such as for example TWEEN80, THF or ether are added to the reaction mixture.

In one embodiment, solvent and/or surfactants such as for example TWEEN80, THF or ether are mixed with ambradiol prior to its incorporation into the reaction mixture.

In one embodiment, the reaction mixture is mixed or homogenized using methods known to the art, preferably using ultrasonication.

One advantage of cyclodehydration in water using a solid catalyst such as for example montmorillonite clay is that there is no need for consumable chemicals other than water, the reaction can be run without the use of an organic solvent even in the case of Non-Soluble Diols such as ambradiol and separation can be performed easily, especially in the case of (−)ambrafuran.

In one embodiment, the reaction is allowed to run for between 1 hour and 72 hours, preferable between 15 and 24 hours.

In another embodiment, the solid catalyst, preferably montmorillonite catalyst, is reused following the cyclization reaction.

In again another embodiment, (−)ambrafuran is removed from the reaction mixture by filtration, decanting, centrifugation, supercritical fluid extraction or solvent extraction, preferably using a supercritical fluid.

In one embodiment, (−)ambrafuran is produced with at least 78% purity, preferably over 85% purity, more preferably over 98% purity.

II.4. High-Temperature Water (HTW) Conditions, Potentially Combined with a Solid Catalyst Such as for Example Montmorillonite Clays According to one embodiment, the process of the invention is performed in HTW at HTW temperature and pressure conditions. In one embodiment, the temperature is higher than 80° C., preferably is ranging from 110° C. to 200° C., preferably from 130 to 170° C. In one embodiment, the pressure is ranging from 0.001 to 350 bars, preferably from 0.1 to 70 bars, more preferably from 1.5 to 15 bars. In another embodiment, the pressure is ranging from 1 to 30 bars, preferably from 2 to 10 bars, more preferably is about 5 bars. In one embodiment, water is brought to HTW conditions or close to HTW conditions in a pre-heating vessel prior to contacting ambradiol.

In one embodiment, water is brought to HTW conditions or close to HTW conditions in a pre-heating vessel prior to contacting ambradiol.

In one embodiment, prior to performing the cyclodehydration reaction, water is degassed using methods known to the art. In another embodiment, water is not degassed.

In one embodiment, $CO_2$ and/or $N_2$ and/or air or other gases or fluids and/or a cosolvent such as ethanol or tetrahydrofuran is/are added to the reaction mixture.

In one embodiment, the reaction mixture is mixed or homogenized using methods known to the art, preferably using ultrasonication. In one embodiment, such mixing is achieved using a static mixer.

In one embodiment, solvent and/or surfactants such as for example TWEEN80, THF or ether are added to the reaction mixture.

In one embodiment, solvent and/or surfactants such as for example TWEEN80, THF or ether are mixed with ambradiol prior to its incorporation into the reaction mixture.

In one embodiment, ambradiol is heated up to about 120° C. prior to being added to HTW.

In one embodiment, $CO_2$ and/or $N_2$ are under supercritical conditions thereby forming an expanded liquid with ambradiol.

In one embodiment, additives such as Lewis or Bronsted acids are added to the reaction mixture.

According to one embodiment, cyclodehydration is performed in a vessel optionally packed with a solid acid catalyst such as for example silica or a zeolite or a K-type montmorillonite, preferably a K10 montmorillonite.

In one embodiment, when a solid catalyst such as for example K-type montmorillonites are added to the reaction mixture, total water content of the reaction mixture is ranging from 3% to 99.9%, preferably from 50% to 80%, more preferably from 60% to 70%.

One advantage of cyclodehydration in HTW is that conditions are compatible with a continuous process, especially a process using supercritical or near-critical fluids, do not require the use of consumable chemicals other than water and do not require the use of organic solvents when the substrate is not soluble in HTW such as ambradiol.

In one embodiment, following cyclodehydration, the mixture exiting the HTW reactor comprising HTW and (−)ambrafuran, is transferred into a collection vessel before being extracted or separated by conventional means including centrifugation, drying or filtration but preferably using a supercritical fluid, more preferably using supercritical $CO_2$.

According to one embodiment, the (−)ambrafuran-charged HTW contained in the collection vessel is transferred to a separator vessel where pressure is lowered, thereby causing the HTW to turn into steam. Steam can then be extracted from the vessel by conventional means, thereby leaving (−)ambrafuran virtually free of water.

In one embodiment, ambrafuran is (−)ambrafuran in at least 78% purity, preferably over 90% purity, more preferably over 98% purity.

II.5. Preferred Method of Manufacturing of (−)-Ambrafuran

A preferred embodiment the manufacturing of sclareolide, ambradiol and/or (−)-ambrafuran starting from sclareol is the following:

In a first step of the process of the present invention, ambradiol produced by biological conversion of sclareol is extracted by supercritical $CO_2$ extraction from the bioconversion broth.

The supercritical fluid containing ambradiol and optionally water from the bioconversion broth may then be directly used in a step of dehydration to synthesize (−)-ambrafuran.

Advantageously, dehydration to (−)ambrafuran may be catalyzed by the use of HTW, optionally in the presence of a solid catalyst such as for example K-type montmorillonites.

Alternatively, dehydration to (−)-ambrafuran may also be conducted by reacting ambradiol with a solid catalyst such as for example K-type montmorillonites in water medium.

It was also found that dehydration was possible in HTW, in a pressured vessel, also using supercritical $CO_2$. Moreover, it was discovered that this reaction may occur without previous purification of sclareolide and/or ambradiol.

III. Device

This invention also pertains to a device for implementing a process according to the present invention.

In one embodiment, the device for implementing a of the invention comprises a pressured vessel which may be packed with a solide catalyst, such as for example montmorillonite, the pressured vessel being preferably associated with a heating device capable of heating the walls of the vessel.

EXAMPLES

The present invention is further illustrated by the following examples.

General

Substances Used

Sclareolide: a product of Sigma Aldrich

Ambradiol: synthesized from sclareolide using $LiAlH_4$ in THF under temperature control.

(−)ambrafuran: a product of Sigma Aldrich

Montmorillonite: K5, K10, KP10, KSF/O montmorillonite from Sigma Aldrich, CAS 1318-93-0

Analysis

The products were quantified by chiral gas chromatographic analysis (capillary column Agilent 19091G-B233E HP-Chiral-20B; oven initial temperature: 50° C., oven final temperature: 240° C., inlet initial temperature: 250° C.; inlet detector temperature: 280° C.; pressure: 21.85 psi; carrier gas: helium) followed by mass spectrometry (solvent delay: 3 min; threshold: 300; sample number: 2; A/D samples: 4; MS source: 230 C; MS quad: 150 C; Low/High scan parameters: 40/550) and confirmed, when necessary, using H-NMR and/or C-NMR. Depending on sample, NMR spectra were recorded in a Bruker Avance II 300 spectrometer. 1H measurements was done in 300 MHz at 300 K, 13 C measurement was done in 75 MHz at 300K. The solvent signal (CDCl3) was used as reference. Other samples were analyzed with a Bruker UltraShield Plus 400 MHz spectrometer, 1H measurements were carried out in 400 MHz at 300 K.

Example 1

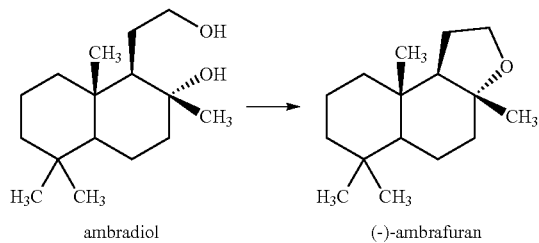

Scheme 5 ambradiol → (-)-ambrafuran

Ambradiol was converted into (-)-ambrafuran (scheme 5) in presence of HTW using $CO_2$ for pressure control with prior water degassing.

Figures 5, 6:
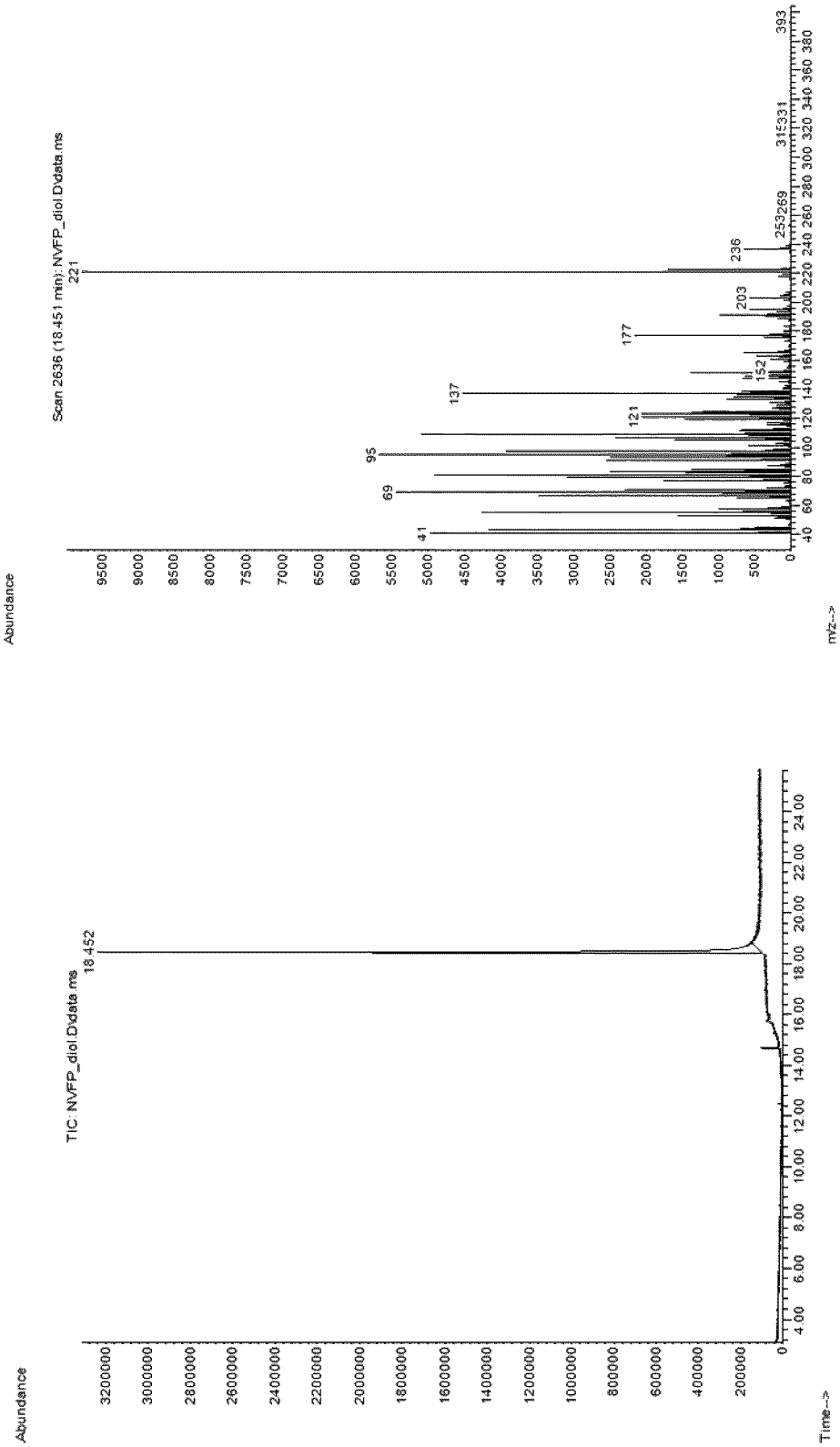
FIG. 5 is a Gas Chromatography (GC) of standard ambradiol.
FIG. 6 is a Mass Spectra (MS) of standard ambradiol.
Figures 7, 8:
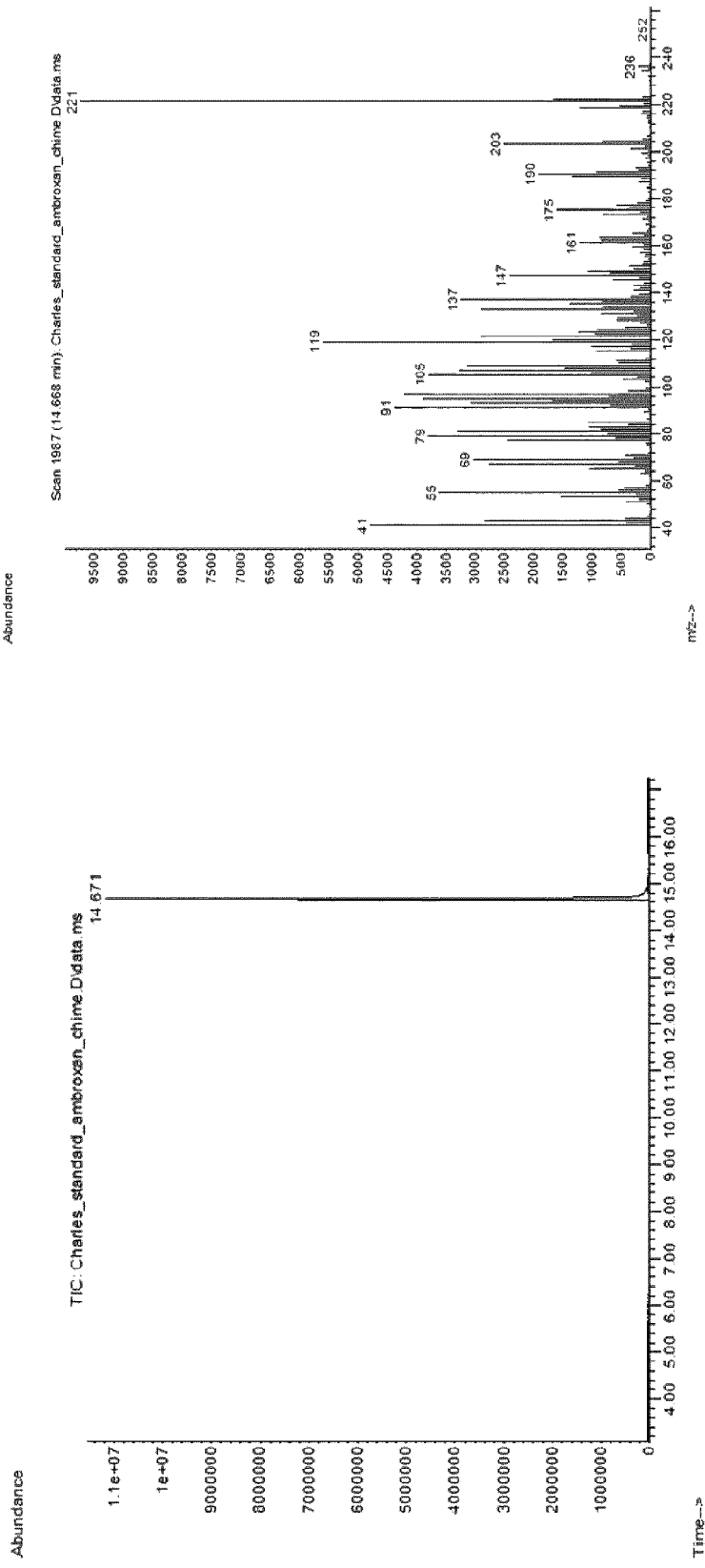
FIG. 7 is a Gas Chromatography (GC) of standard (−)ambrafuran.
FIG. 8 is a Mass Spectra (MS) for standard (−)ambrafuran.
Figures 9, 10:
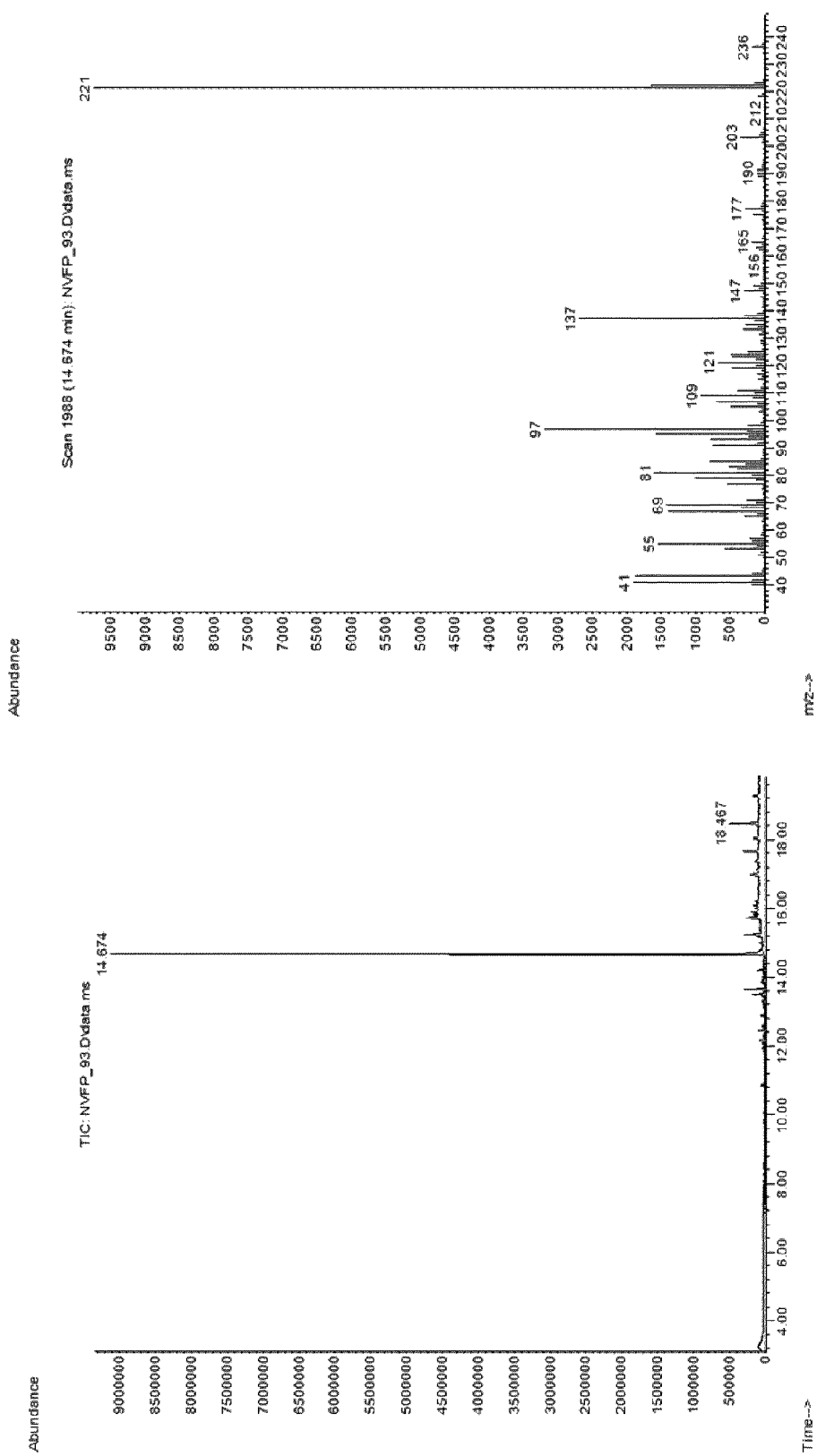
FIG. 9 is a Gas Chromatography (GC) of the reaction mixture obtained for the cyclodehydration of ambradiol into ambrafuran in presence of HTW using CO2 for pressure control with prior water degassing (Example 1).
FIG. 10 is a Mass Spectra (MS) of the reaction mixture obtained for the cyclodehydration of ambradiol into ambrafuran in presence of HTW using CO2 for pressure control with prior water degassing (Example 1).

12 ml distilled water was mixed with 100 mg ambradiol in a 300 ml pressure reactor in stainless steel. After initial degassing using CO2, 1.5 bars of $CO_2$ pressure was applied and temperature was raised to 150° C., which caused the system pressure to reach 7 bars. System parameters were maintained and mixture was stirred at 500 rpm for 3.5 hours. At the end of the experiment, products were extracted from the mixture and dried in rotavapor. Chromatograph and mass spectra (FIGS. 9 and 10) were compared to that of standard (-)ambrafuran (FIGS. 7 and 8) and standard ambradiol (FIGS. 5 and 6).

This experiment produced a conversion yield of 92.5% with 100% selectivity to (-)ambrafuran. No isomer of (-)ambrafuran was detected.

Example 2

Ambradiol was converted into (-)-ambrafuran (scheme 5) in presence of HTW using $CO_2$ for pressure control with no prior water degassing.

Figures 11, 12:
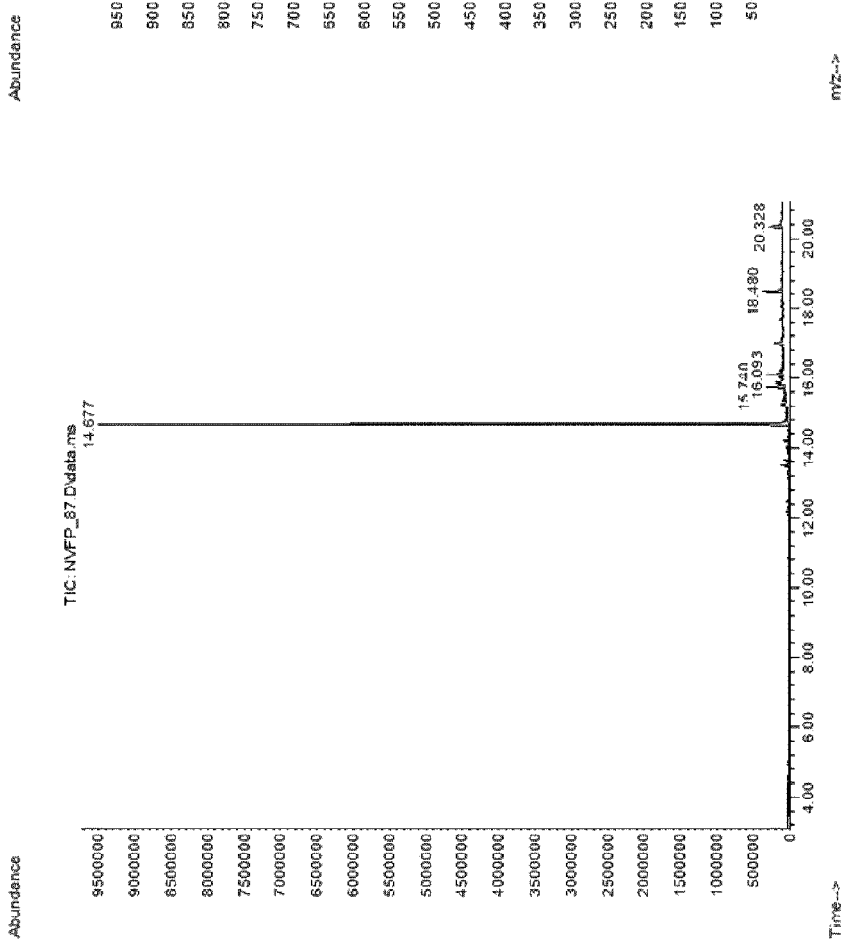
FIG. 11 is a Gas Chromatography (GC) of the reaction mixture obtained for the cyclodehydration of ambradiol into ambrafuran in presence of HTW using CO2 for pressure control with no prior water degassing (Example 2).
FIG. 12 is a Mass Spectra (MS) of the reaction mixture obtained for the cyclodehydration of ambradiol into ambrafuran in presence of HTW using CO2 for pressure control with no prior water degassing (Example 2).

15 ml distilled water was mixed with 100 mg ambradiol in a 300 ml pressure reactor in stainless steel. 1 bar of $CO_2$ pressure was applied and temperature was raised to 140° C., which caused the system pressure to reach 5.2 bars. System parameters were maintained and mixture was stirred at 500 rpm for 2 hours. At the end of the experiment, products were extracted from the mixture and dried in rotavapor. Chromatograph and mass spectra (FIGS. 11 and 12) were compared to that of standard (-)ambrafuran (FIGS. 7 and 8) and standard ambradiol (FIGS. 5 and 6).

This experiment produced a conversion yield of 91.3% with 87.45% selectivity to (-)ambrafuran while the remaining 12.55% consisted of oxidation products of ambradiol, primarily aldehyde and carboxylic acid-ambradiol derivatives that were confirmed using NMR. No isomer of (-)ambrafuran was detected.

Figure 13:
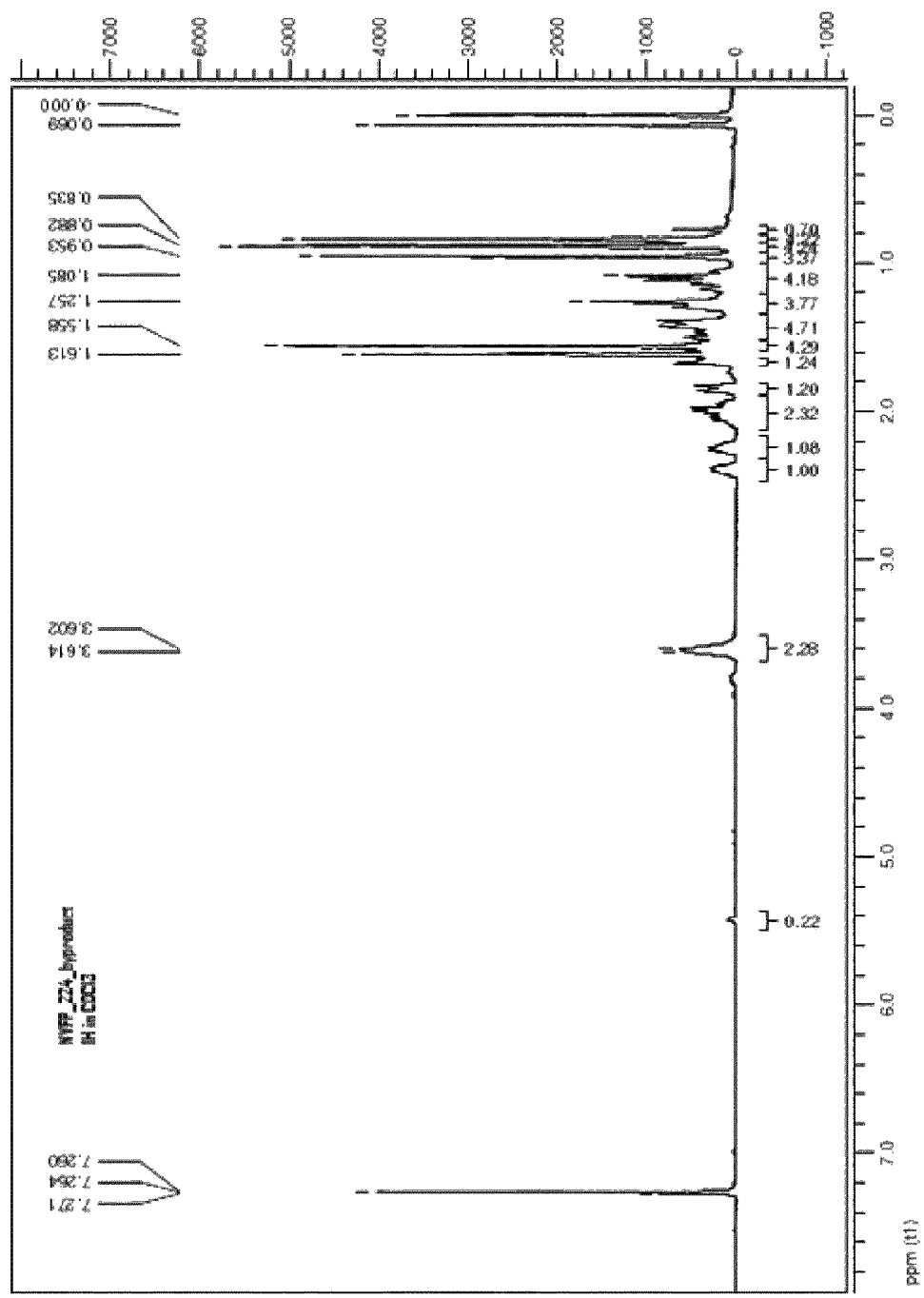
FIG. 13 is an NMR spectra of one of the by-products from Example 2.
Figure 14:
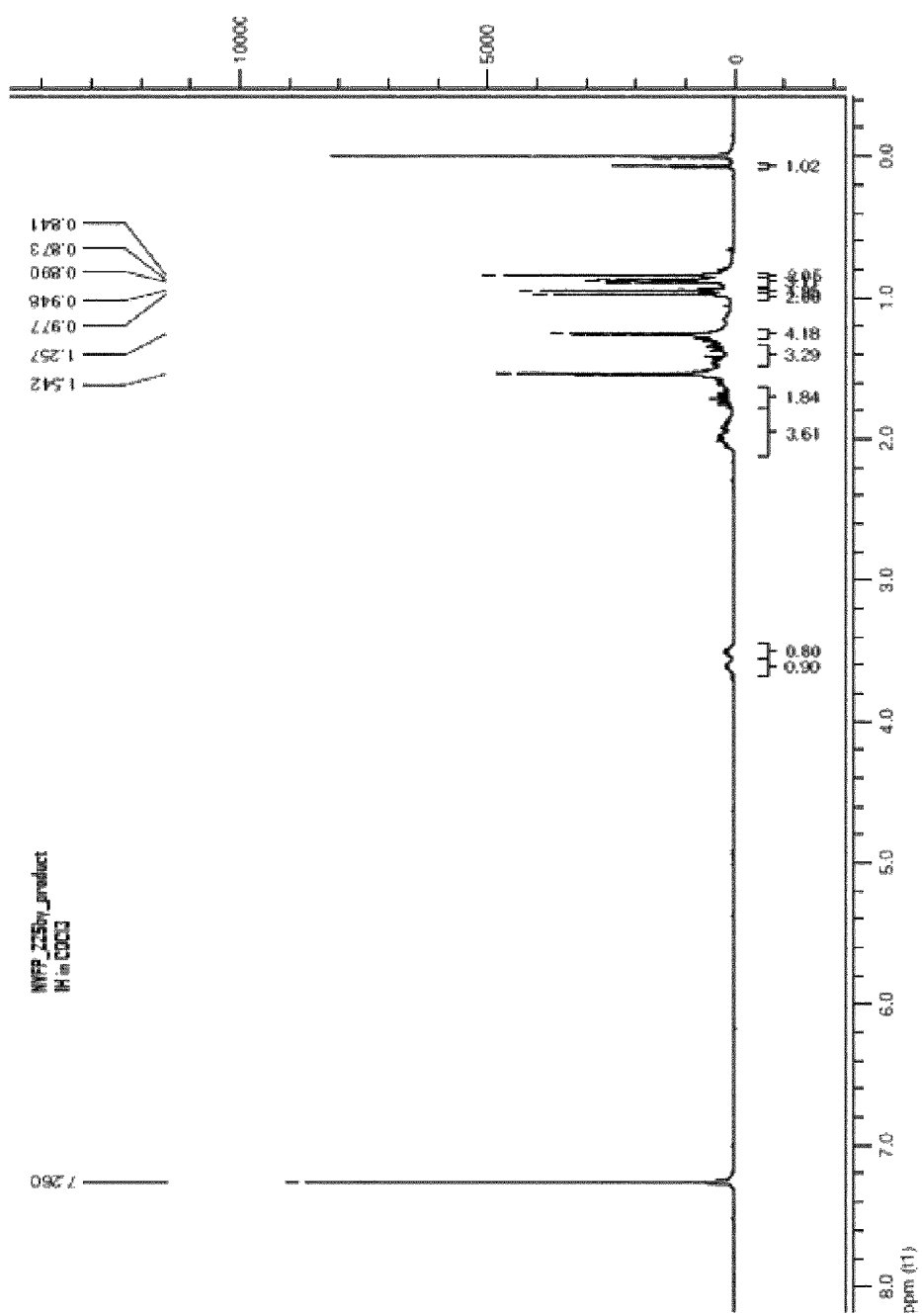
FIG. 14 is an NMR spectra of one of the by-products from Example 2.

The NMR spectras of by-products obtained in this example are represented on FIGS. 13 and 14.

Example 3

In order to test the rehydration and isomerization of (-)ambrafuran in HTW, (-)ambrafuran was subjected to HTW (scheme 5) using $CO_2$ for pressure control with no prior water degassing.

Figures 15, 16:
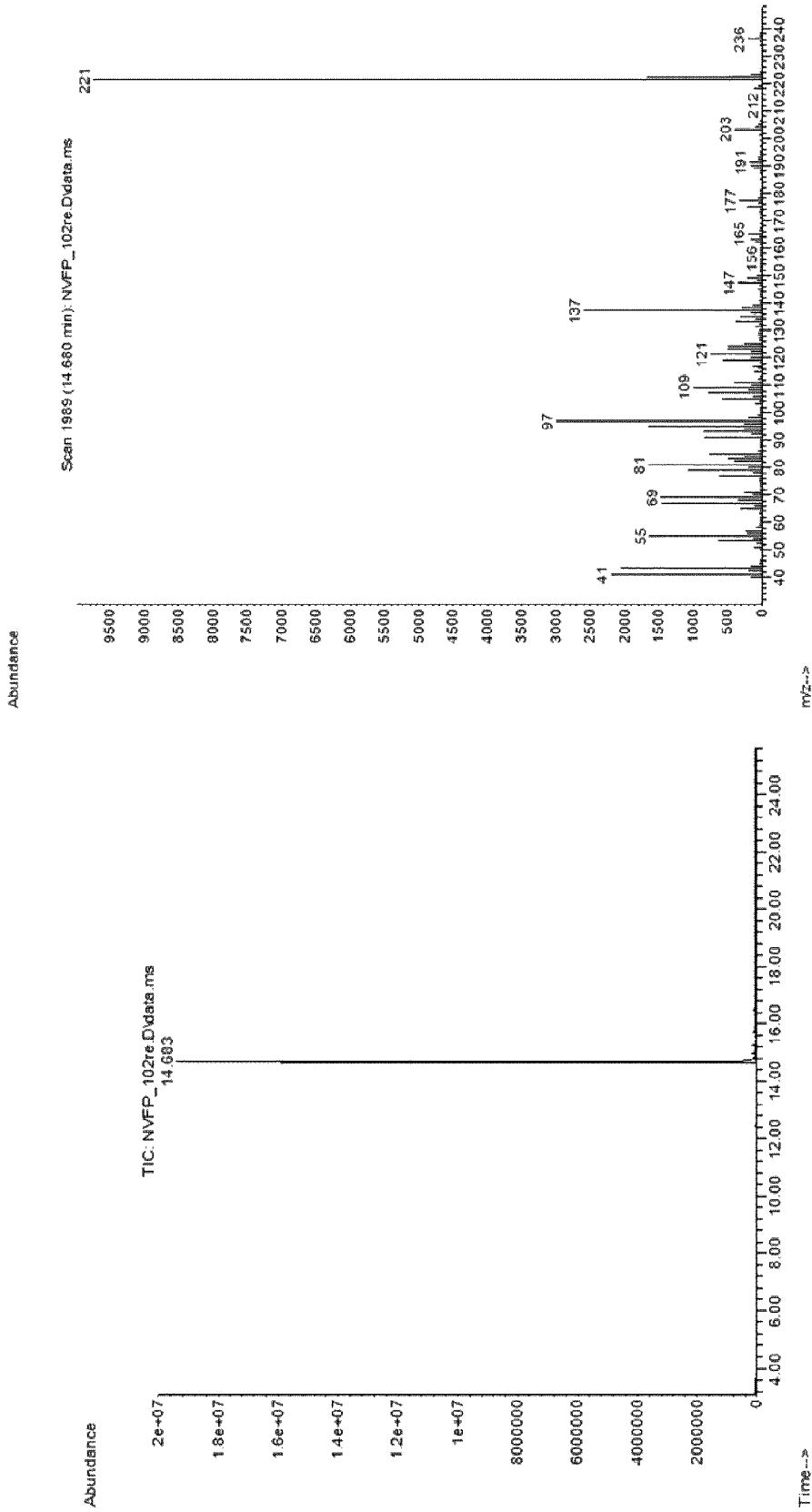
FIG. 15 is a Gas Chromatography (GC) of the reaction mixture obtained from Example 3.
FIG. 16 is an Mass Spectra (MS) of the main compound obtained from Example 3.

12 ml distilled water was mixed with 100 mg (-)ambrafuran in a 300 ml pressure reactor in stainless steel. 1.2 bars of $CO_2$ pressure was applied and temperature was raised to 150° C., which caused the system pressure to reach 6.5 bars. System parameters were maintained and mixture was stirred at 500 rpm for 2 hours. At the end of the experiment, products were extracted from the mixture and dried in rotavapor. Chromatograph and mass spectra (FIGS. 15 and 16) were compared to that of standard (-)ambrafuran (FIGS. 7 and 8) and standard ambradiol (FIGS. 5 and 6).

No conversion was observed.

Example 4

Ambradiol was converted into (-)-ambrafuran (scheme 5) in presence of HTW using $N_2$ for pressure control with prior water degassing.

Figures 17, 18:
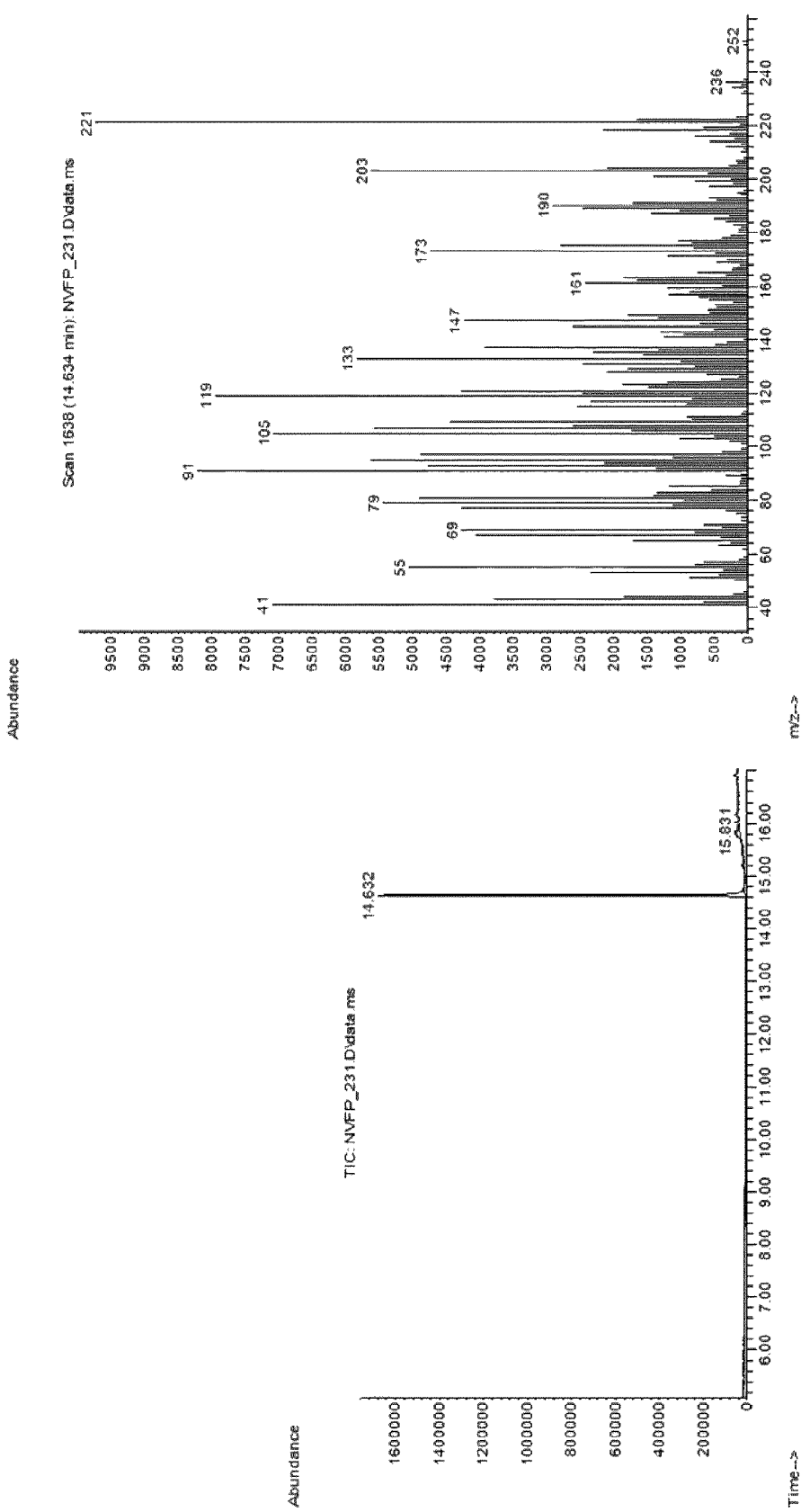
FIG. 17 is Gas Chromatography (GC) of the reaction mixture obtained for the cyclodehydration of ambradiol into ambrafuran in presence of HTW using N2 for pressure control with no prior water degassing (Example 4).
FIG. 18 is an Mass Spectra (MS) of the reaction mixture obtained for the cyclodehydration of ambradiol into ambrafuran in presence of HTW using N2 for pressure control with no prior water degassing (Example 4).

15 ml distilled water was mixed with 100 mg ambradiol in a 300 ml pressure reactor in stainless steel. 6 bar of $CO_2$ pressure was applied and temperature was raised to 150° C., which caused the system pressure to reach 10 bars. System parameters were maintained and mixture was stirred at 500 rpm for 2 hours. At the end of the experiment, products were extracted from the mixture and dried in rotavapor. Chromatograph and mass spectra (FIGS. 17 and 18) were compared to that of standard (-)ambrafuran (FIGS. 7 and 8) and standard ambradiol (FIGS. 5 and 6).

This experiment produced a conversion yield of close to 100% with 98.42% selectivity to (-)ambrafuran while the remaining 1.58% consisted of oxidation products of ambradiol, primarily aldehyde and carboxylic acid-ambradiol derivatives. No isomer of (-)ambrafuran was detected.

Example 5

Ambradiol was converted into (-)-ambrafuran (scheme 5) in presence of a K10 montmorillonite in water medium.

10 ml distilled water was mixed with 100 mg ambradiol and 400 mg K10 montmorillonite in a glass container and temperature was raised to 40° C. System parameters were maintained and mixture was stirred at 150 rpm for 30 hours. At the end of the experiment, products were extracted from the mixture and dried in rotavapor.

Figures 19, 20:
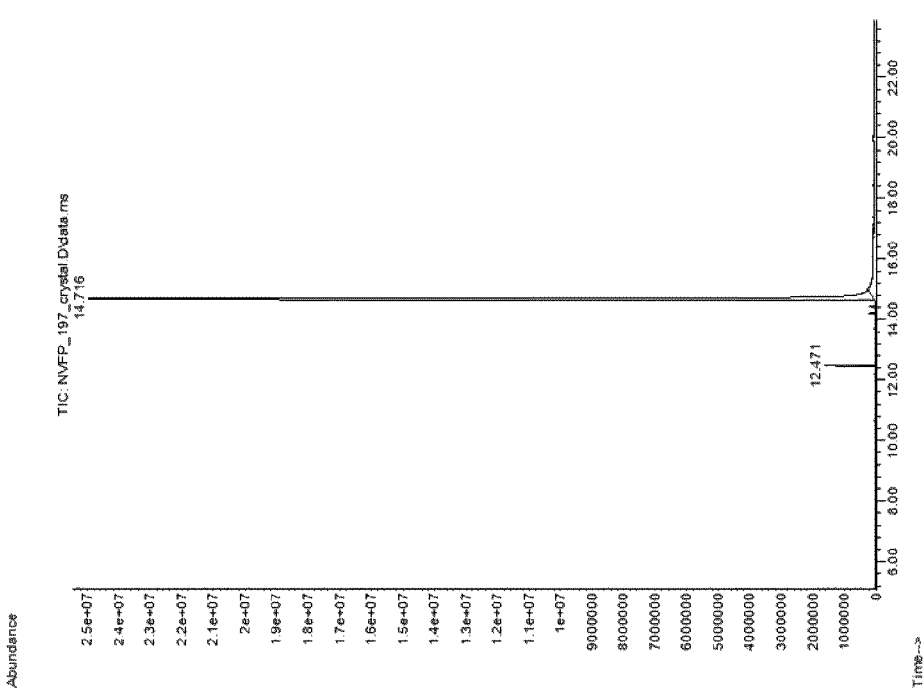
FIG. 19 is a Gas Chromatography (GC) of the reaction mixture obtained for the cyclodehydration of ambradiol into ambrafuran in presence of K10 montmorillonite in water medium (Example 5).
FIG. 20 is an Mass Spectra (MS) of the reaction mixture obtained for the cyclodehydration of ambradiol into ambrafuran in presence of K10 montmorillonite in water medium (Example 5).

Chromatograph and mass spectra (FIGS. 19 and 20) were compared to that of standard (-)ambrafuran (FIGS. 7 and 8) and standard ambradiol (FIGS. 5 and 6).

Figure 21:
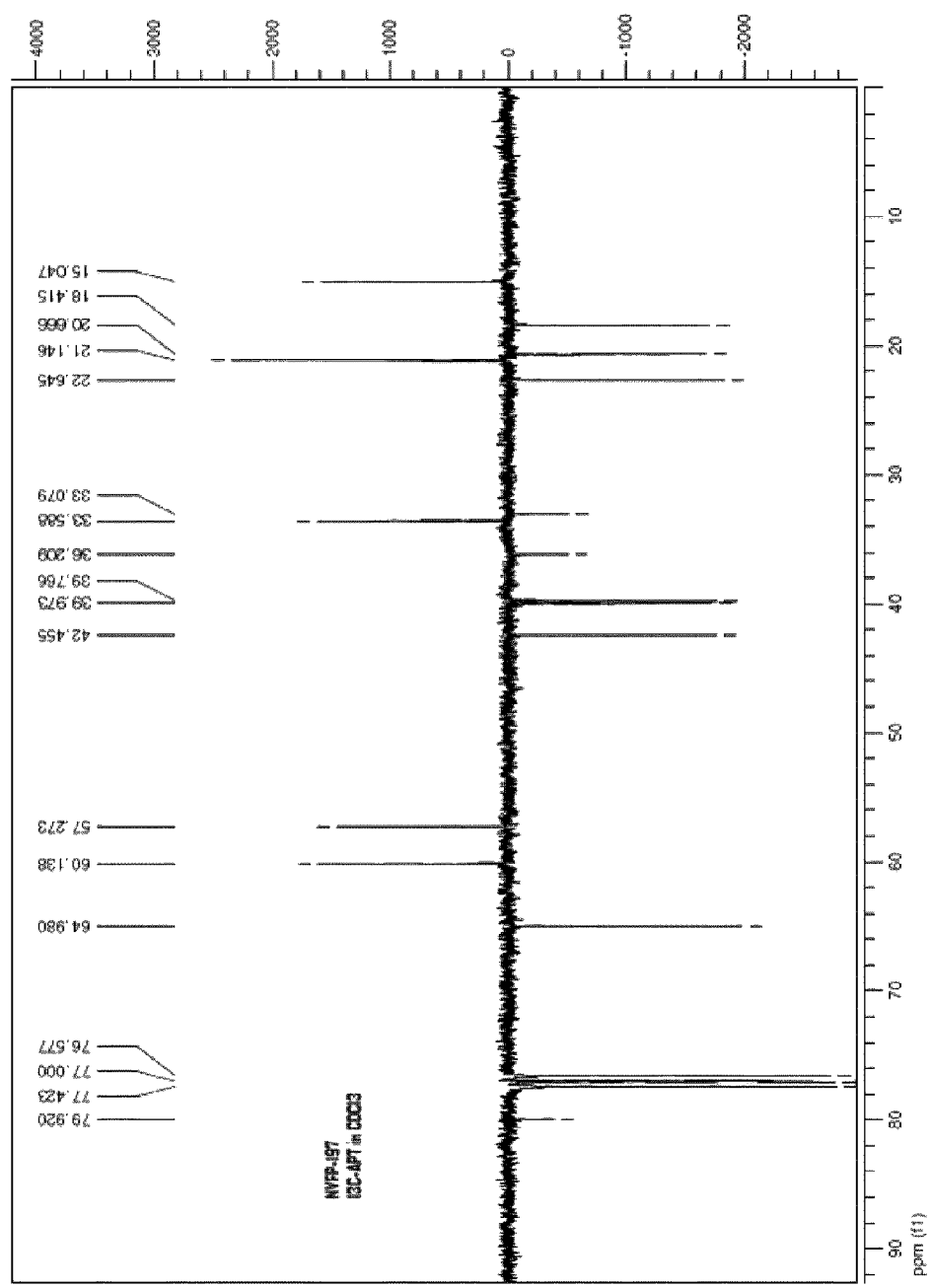
FIG. 21 is an NMR spectra of the main product from Example 5.

The NMR spectra of the main compound obtain in this example is represented on FIG. 21 and corresponds to ambrafuran.

This experiment produced a conversion yield of 100% with 98% selectivity to (-)ambrafuran. No isomer of (-)ambrafuran was detected.

Example 6

Ambradiol was subjected to HTW (scheme 5) in the presence of a K10 montmorillonite, using $CO_2$ for pressure control with no prior water degassing.

Figures 22, 23:
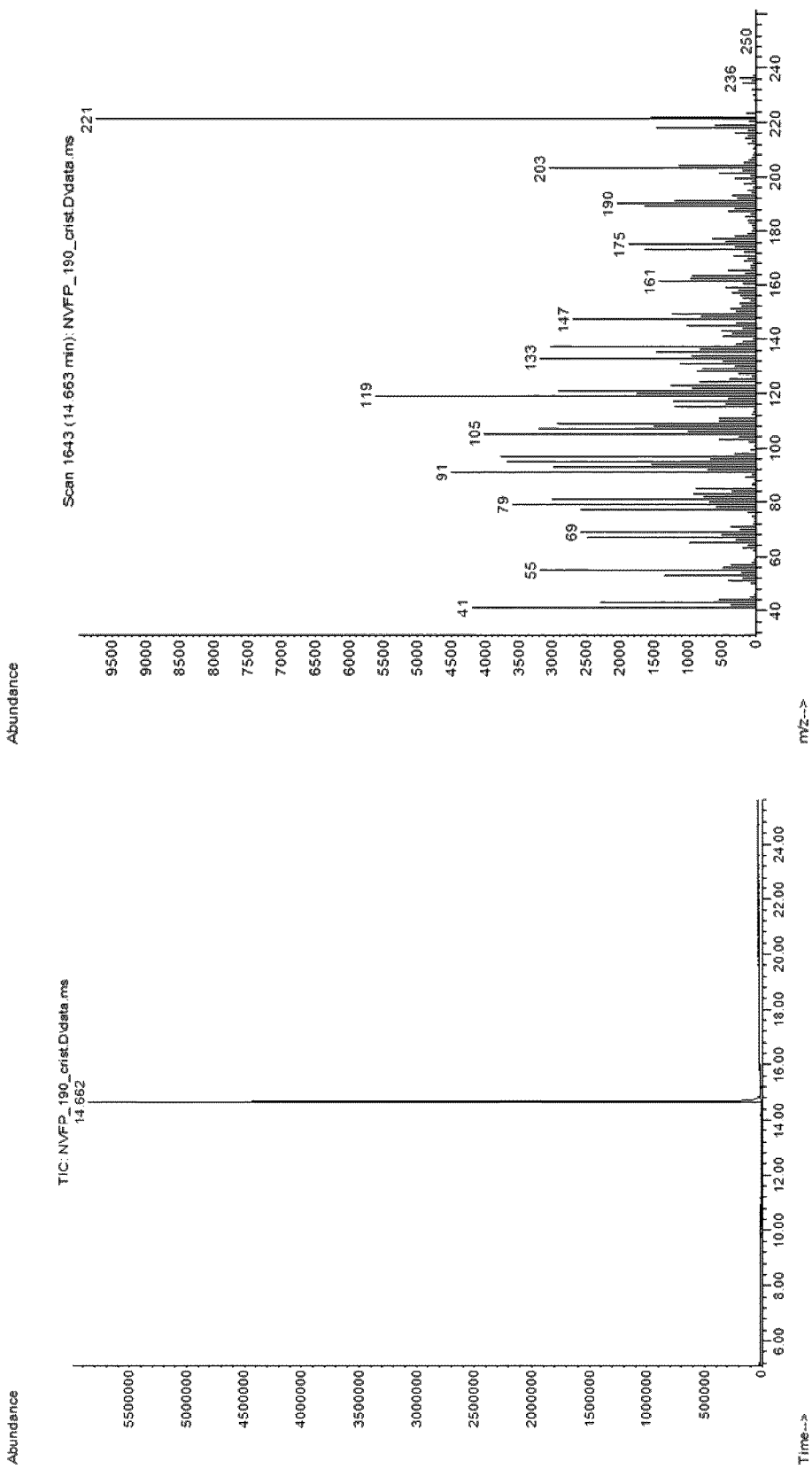
FIG. 22 is a Gas Chromatography (GC) of the reaction mixture obtained for the cyclodehydration of ambradiol into ambrafuran in presence of HTW and K10 montmorillonite using CO2 for pressure control with no prior water degassing (Example 6)
FIG. 23 is an Mass Spectra (MS) of the reaction mixture obtained for the cyclodehydration of ambradiol into ambrafuran in presence of HTW and K10 montmorillonite using CO2 for pressure control with no prior water degassing (Example 6).

10 ml distilled water was mixed with 100 mg ambradiol and 400 mg K10 montmorillonite in a 300 ml pressure reactor in stainless steel. 1 bar of $CO_2$ pressure was applied and temperature was raised to 120° C., which caused the system pressure to reach 3 bars. System parameters were maintained and mixture was stirred at 150 rpm for 15 minutes. At the end of the experiment, products were extracted from the mixture and dried in rotavapor. Chromatograph and mass spectra (FIGS. 22 and 23) were compared to that of standard (−)ambrafuran (FIGS. 7 and 8) and standard ambradiol (FIGS. 5 and 6).

Figure 24:
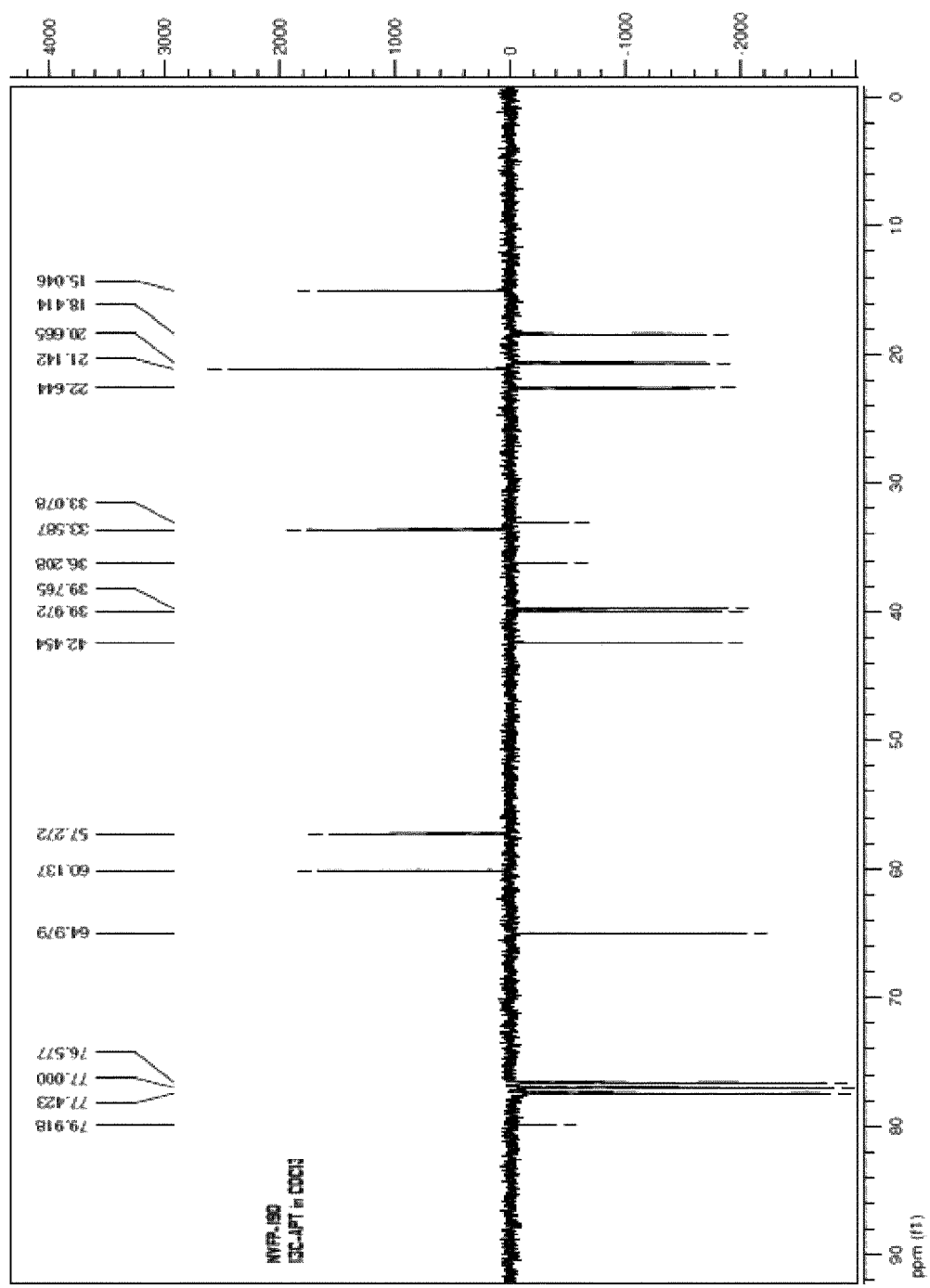
FIG. 24 is an NMR spectra of the main product from Example 6.

The NMR spectra of the main compound obtain in this example is represented on FIG. 24 and corresponds to ambrafuran.

This experiment produced a conversion yield close to 100% with about 98% selectivity to (−)ambrafuran. No isomer of (−)ambrafuran was detected.

Examples 7, 8, 9 and 10

Example 5 was repeated using respectively K5, KP10, KSF/O montmorillonites and the K10 catalyst used in example 5 with no prior recharging.

These experiments all produced a yield close to 100%% with about 98% conversion selectivity to (−)ambrafuran. No isomer of (−)ambrafuran was detected.

Example 11

This experiment aimed at extracting ambradiol from a bioconversion broth using supercritical CO2.

Ambradiol was produced from sclareol using the organism Hyphozyma Roseonigra, ATCC 20624. Biological conversion took place in a 1.5 L aqueous bioconversion broth using methods known to the art. The bioconversion resulted in the transformation of 4 g/L of sclareol with a conversion yield or 98%, of which 99% was ambradiol and 1% was sclareolide. After conversion was complete, the broth was subjected to supercritical CO2 extraction at 35° C. and 150 bars without cosolvent with a 4 kg/h CO2 flow rate.

After 7 hours of extraction, the experiment was stopped. Extracts collected in the separator were dried and analyzed showing a concentration of 1.5% sclareol and 98.5% ambradiol. Only traces of sclareolide were found in the bioconversion broth after extraction. No ambradiol was found in the bioconversion broth.

Example 12

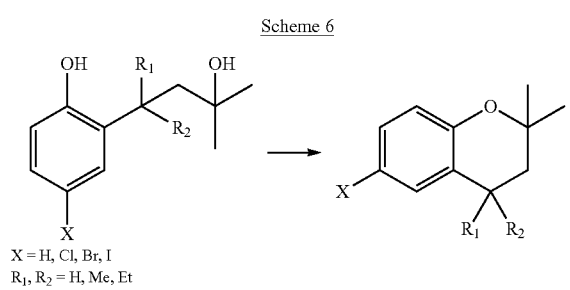

Scheme 6

X = H, Cl, Br, I
R1, R2 = H, Me, Et

The above transformation of a chroman derivative was performed in presence of HTW using $N_2$ for pressure control with prior water degassing (scheme 6).

15 ml distilled water was mixed with 100 mg substrate in a 300 ml pressure reactor in stainless steel. 6 bars of $CO_2$ pressure was applied and temperature was raised to 150° C., which caused the system pressure to reach 10 bars. System parameters were maintained and mixture was stirred at 500 rpm for 2.5 hours. At the end of the experiment, products were extracted from the mixture and dried in rotavapor. Chromatograph and mass spectra were compared to that of standard product.

This experiment produced a conversion yield of close to 100% with over 95% selectivity to the targeted product.

Example 13

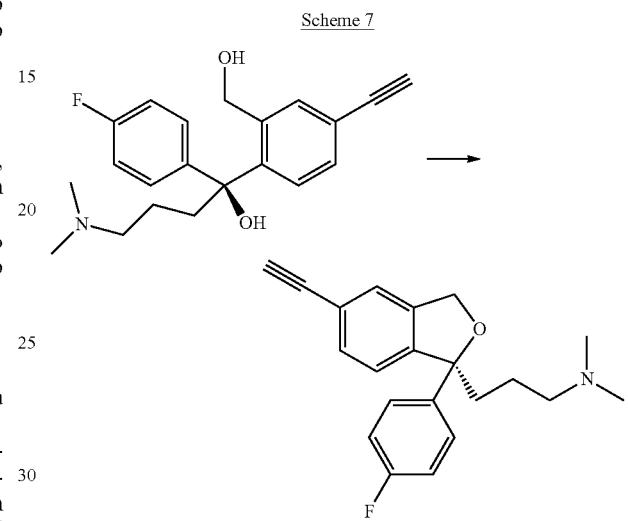

Scheme 7

The above transformation of escitalopram was performed in presence of HTW using $N_2$ for pressure control with prior water degassing (scheme 7).

15 ml distilled water was mixed with 100 mg substrate in a 300 ml pressure reactor in stainless steel. 6 bars of $CO_2$ pressure was applied and temperature was raised to 150° C., which caused the system pressure to reach 10 bars. System parameters were maintained and mixture was stirred at 500 rpm for 2.5 hours. At the end of the experiment, products were extracted from the mixture and dried in rotavapor. Chromatograph and mass spectra were compared to that of standard product.

This experiment produced a conversion yield of close to 100% with over 97% selectivity to the targeted product.

The invention claimed is:

1. A process for the stereoselective synthesis of chiral cycloether derivatives from chiral diols comprising:
   (i) stereoselective cyclodehydration in water of 1,4- or 1,5-diols comprising at least one chiral tertiary alcohol functional group with retention of the initial chirality, and/or
   (ii) cyclodehydration in water of 1,4- or 1,5-diols, said diols being non-miscible with and/or non-soluble in water,
   into corresponding cycloether derivatives, said process comprising:
   bringing a reaction mixture of (i) higher than 3% (w/w) of water and 1,4- or 1,5-diols comprising at least one chiral tertiary alcohol functional group with retention of the initial chirality and/or (ii) water and 1,4- or 1,5-diols, said diols being non-miscible with and/or non-soluble in water, to high temperature water (HTW) conditions with a temperature from 80° C. to 380° C.; and/or mixing a reaction mixture of (i) water and 1,4- or 1,5-diols comprising at least one chiral tertiary alcohol functional group with retention of the initial chirality and/or (ii) water and 1,4- or 1,5-diols, said diols being non-miscible with and/or non-soluble in water with a solid catalyst at a temperature from room temperature up to 380° C.

2. The process according to claim 1, wherein the cycloether derivative is of general formula (IIa) or (IIb)

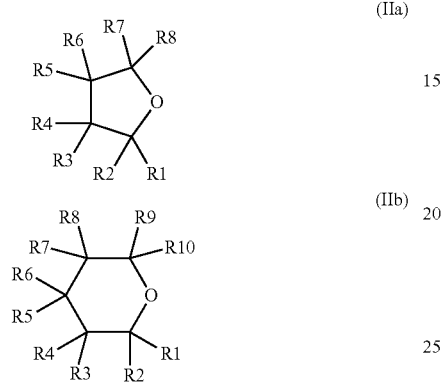

wherein:
  R1 and R2 are the same or different and are selected from optionally substituted groups selected from the group consisting of alkyl, alkenyl, alkynyl, cycloalkyl, cycloalkenyl, aryl, and an heterocyclic group, or R1 and R2 form a substituted or unsubstituted ring with R3 or R4, or form together a substituted or unsubstituted ring,
  R3 and R4 are the same or different and are an hydrogen atom or selected from optionally substituted groups selected from the group consisting of alkyl, alkenyl, alkynyl, cycloalkyl, cycloalkenyl, aryl, and an heterocyclic group, or R3 and R4 form a substituted or unsubstituted ring with R1 or R2 and/or with R5 or R6, or form together a substituted or unsubstituted ring,
  R5 and R6 are the same or different and are an hydrogen atom or selected from optionally substituted groups selected from the group consisting of alkyl, alkenyl, alkynyl, cycloalkyl, cycloalkenyl, aryl, and an heterocyclic group, or R5 and R6 form a substituted or unsubstituted ring with R3 or R4 and/or with R7 or R8 when applicable, or form together a substituted or unsubstituted ring,
  R7 and R8 are the same or different and are an hydrogen atom or selected from optionally substituted groups selected from the group consisting of alkyl, alkenyl, alkynyl, cycloalkyl, cycloalkenyl, aryl, and an heterocyclic group, or R7 and R8 form a substituted or unsubstituted ring with R5 or R6 and/or with R9 or R10 when applicable, or form together a substituted or unsubstituted ring, and
  R9 and R10 are the same or different and are an hydrogen atom or selected from optionally substituted groups selected from the group consisting of alkyl, alkenyl, alkynyl, cycloalkyl, cycloalkenyl, aryl, and an heterocyclic group, or R9 and R10 form a substituted or unsubstituted ring with R7 or R8, or form together a substituted or unsubstituted ring; and
  the process comprises cyclodehydration of respectively a 1,4- or 1,5-diol of general formula (Ia) or (Ib)

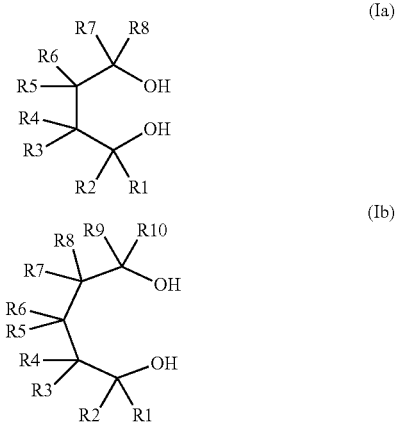

wherein R1, R2, R3, R4, R5, R6, R7, R8, R9 and R10 are as described above.

3. The process according to claim 2, wherein R1 and R2 are different, the corresponding alcohol functional group being a chiral tertiary alcohol functional group.

4. The process according to claim 1, wherein the solid catalyst is a montmorillonite.

5. The process according to claim 1, wherein the 1,4-diol is ambradiol and wherein the cycloether derivative is ambrafuran, preferably (−)-ambrafuran.

6. The process according to claim 5, further comprising a preliminary step of biological conversion of sclareol into ambradiol.

7. The process according to claim 6, wherein ambradiol is purified using supercritical extraction.

8. The process according to claim 6, wherein in the step of biological conversion, sclareol is contacted with a microorganism capable of converting it into sclareolide or ambradiol, said microorganism being in an aqueous nutrient medium.

9. The process according to claim 8, wherein the microorganism is selected from the group consisting of *Cryptococcus albidus* saito, skinner var. *albidus*, ATCC 20918 and *Cryptococcus albidus*, ATCC 20921, and is capable to convert sclareol into sclareolide.

10. The process according to claim 8, wherein the microorganism is selected from the group consisting of *Hyphozyma roseoniger* (CBS214.83 and ATCC 20624).

11. The process according to claim 5, further comprising a preliminary step of biological conversion of sclareol into sclareolide.

12. The process according to claim 11, wherein sclareolide is purified using supercritical extraction.

13. The process according to claim 5, wherein the process is continuous or semi-continuous.

14. The process according to claim 1, wherein the HTW conditions include a temperature from 110° C. to 200° C.

15. The process according to claim 1, wherein a temperature from room temperature up to 80° C. is implemented when a solid catalyst is included in the reaction mixture.

* * * * *